United States Patent [19]

Lürrssen et al.

[11] 4,452,625

[45] Jun. 5, 1984

[54] SYNERGISTIC COMPOSITIONS FOR INHIBITING PLANT GROWTH

[75] Inventors: Klaus Lürssen, Bergisch-Gladbach; Graham Holmwood, Wuppertal; Wolfgang Krämer, Wuppertal; Erik Regel, Wuppertal; Wolf Reiser, Wuppertal; Rolf Schröder, Wuppertal, all of Fed. Rep. of Germany

[73] Assignee: Bayer Aktiengesellschaft, Leverkusen, Fed. Rep. of Germany

[21] Appl. No.: 337,648

[22] Filed: Jan. 7, 1982

[30] Foreign Application Priority Data

Jan. 27, 1981 [DE] Fed. Rep. of Germany ....... 3102588

[51] Int. Cl.³ ...................... A01N 43/64; A01N 37/00

[52] U.S. Cl. ........................................... 71/76; 71/86; 71/92; 71/106; 71/113

[58] Field of Search ...................... 71/92, 106, 113, 76

[56] References Cited

FOREIGN PATENT DOCUMENTS

| | | | |
|---|---|---|---|
| 0005600 | 11/1979 | European Pat. Off. | 71/92 |
| 0005782 | 12/1979 | European Pat. Off. | 71/106 |
| DT2407143 | 8/1975 | Fed. Rep. of Germany . | |
| DT2645617 | 2/1977 | Fed. Rep. of Germany . | |
| DT2053967 | 4/1977 | Fed. Rep. of Germany . | |
| DE2737489 | 2/1978 | Fed. Rep. of Germany . | |
| DE2838847 | 3/1979 | Fed. Rep. of Germany . | |
| 2906061 | 1/1981 | Fed. Rep. of Germany | 71/92 |
| 2461458 | 3/1981 | France | 71/106 |

OTHER PUBLICATIONS

Res. Disclosure, "Compounds of the, etc.," (1978), Res. Discl., 176, pp. 44–47, (1978).

*Primary Examiner*—Glennon H. Hollrah

*Attorney, Agent, or Firm*—Sprung, Horn, Kramer & Woods

[57] ABSTRACT

A plant growth-inhibiting composition comprising (1)

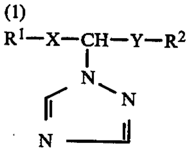

(I)

-continued

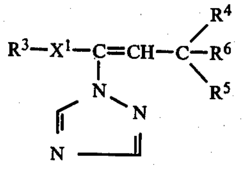

(II)

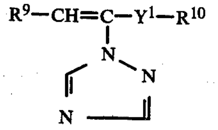

(III)

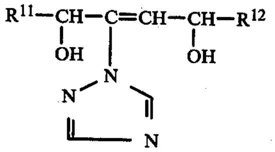

(IV)

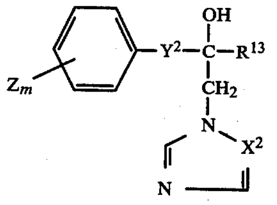

(V)

or

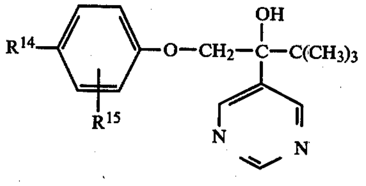

(VI)

and (2)

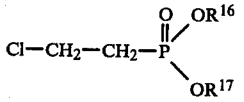

(VII)

or

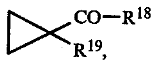

(VIII)

wherein the various radicals are as defined.

6 Claims, No Drawings

SYNERGISTIC COMPOSITIONS FOR INHIBITING PLANT GROWTH

The present invention relates to new plant growth-regulating combinations of certain azoles or pyrimidine butanol derivatives on the one hand and certain known phosphonic acid derivatives or 1-aminocyclopropane-1-carboxylic acid derivatives on the other hand.

It has already been disclosed that numerous triazole derivatives have plant growth-regulating properties (see DE-A (German Published Specification) No. 2,407,143, DE-A (German Published Specification) No. 2,737,489, DE-A (German Published Specification) No. 2,906,061, DE-A (German Published Specification) No. 2,645,617, DE-A (German Published Specification No. 2,838,847 and JP-A (Japanese Published Specification) No. 53,130,661). However, the activity of the substances, especially when small quantities are used, is not always satisfactory.

Furthermore, it is already known that certain pyrimidine butanol derivatives can be used for regulating plant growth (see U.S. application Ser. No. 200,170 filed Oct. 24, 1980, now pending. In many cases, however, the activity of these substances also leaves something to be desired.

It is further known that phosphonic acid derivatives capable of ethylene cleavage affect plant growth (see DE-A (German Published Specification) No. 2,053,967). However, the activity of these substances is also not always adequate in practice.

Finally, it has already been reported that certain 1-amino-cyclopropane-1-carboxylic acid derivatives have plant growth-regulating properties (see U.S. application Ser. No. 192,744 filed Oct. 1, 1980, now pending. However, the results achieved with these substances are also not always completely satisfactory.

According to the present invention there is now provided a new plant growth-regulating composition containing as active ingredients.

(1) an azole of the general formula

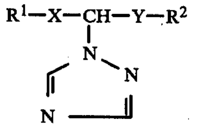

(I)

in which $R^1$ represents an optionally substituted aryl radical, $R^2$ represents an alkyl or halogenoalkyl radical, X represents oxygen or methylene and Y represents carbonyl or a group -CH(OH)- , or an azole of the general formula

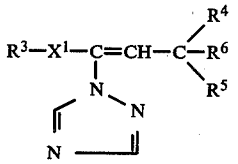

(II)

in which $R^3$ represents an optionally substituted alkyl cycloalkyl or optionally substituted aryl radical, $R^4$ represents a hydrogen atom or an alkyl radical, $R^5$ represents a hydrogen atom or an alkyl, cycloalkyl, optionally substituted cycloalkenyl, alkenyl or optionally substituted aryl radical, or $R^4$ and $R^5$ together with the carbon atom to which they are bonded represent an optionally substituted cycloalkenyl or cycloalkyl radical, $R^6$ represents a hydrogen atom or an alkyl radical, $X^1$ represents a group of the general formula

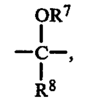

and additionally represents a keto group if $R^3$ represents an optionally substituted alkyl or cycloalkyl radical, $R^7$ represents a hydrogen atom or an alkyl, optionally substituted aralkyl, acyl or optionally substituted carbamoyl radical, and $R^8$ represents a hydrogen atom or an alkyl or optionally substituted aralkyl radical, or an azole of the general formula

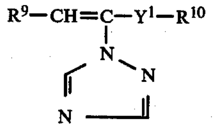

(III)

in which $R^9$ represents an optionally substituted aryl radical, $R^{10}$ represents alkyl, halogenoalkyl or optionally substituted aryl, and $Y^1$ represents carbonyl or a group -CH(OH)-, or an azole of the general formula

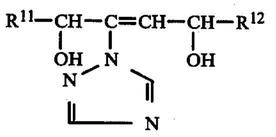

(IV)

in which $R^{11}$ and $R^{12}$ are identical or different and represent an optionally alkyl-substituted cycloalkyl radical, an alkyl or halogenoalkyl radical or a phenyl radical which is optionally substituted by halogen, alkyl, alkoxy, phenyl and/or nitro, or an azole derivative of the general formula

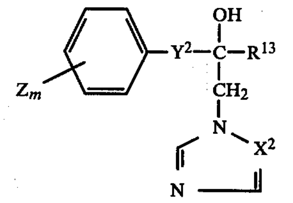

(V)

in which $R^{13}$ represents an alkyl, optionally substituted cycloalkyl or optionally substituted phenyl radical, $X^2$ represents a nitrogen atom or a CH group, $Y^2$ represents a grouping $-OCH_2-$, $-CH_2CH_2-$ or $-CH{=}CH-$, Z represents a halogen or an alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy radical, and m is 0, 1, 2 or 3, or an acid addition salt or metal salt complex of an azole of the formula (I), (II), (III), (IV) or (V), or a pyrimidine butanol derivative of the general formula

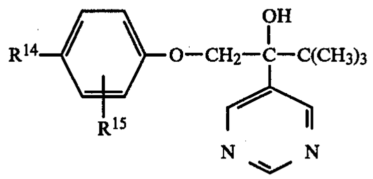

(VI)

in which $R^{14}$ represents a hydrogen or halogen atom or an alkyl or alkoxy radical or a benzyloxy radical which is optionally substituted by halogen, and $R^{15}$ represents a hydrogen or halogen atom, and (2) a phosphoric acid derivative of the general formula

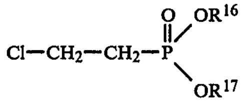

(VII)

in which $R^{16}$ and $R^{17}$ independently of each other represent a hydrogen atom or an alkali metal cation, or a 1-amino-cyclopropane-1-carboxylic acid derivative of the general formula

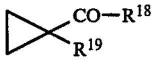

(VIII)

in which $R^{18}$ represents a hydroxyl, alkoxy, aralkoxy, amino, alkylamino or dialkylamino radical or a radical $O^{\ominus}M^{\oplus}$, $M^{\oplus}$ representing an alkali metal ion equivalent or alkaline earth metal ion equivalent, or an ammonium, alkylammonium, dialkylammonium, trialkylammonium or tetraalkylammonium ion, and $R^{19}$ represents an amino radical or a radical —NH—CO—R, wherein R represents a hydrogen atom or an alkyl or aryl radical, and $R^{19}$ further represents a radical $—\overset{\oplus}{N}H_3A^{\ominus}$, wherein $A^{\ominus}$ represents a chloride, bromide or iodide ion, alone or in admixture with a solid or liquid or liquefied gaseous diluent or carrier.

The new active compound combinations of the present invention are very suitable for inhibiting plant growth.

Surprisingly, the plant-growth inhibiting action of the active compound combinations according to the invention is substantially higher than the sum of the actions of the individual active compounds. Thus, a real synergistic effect, which cannot be foreseen, is present, and not only an extension of the action. The active compound combinations thus represent a valuable enrichment of the art.

The formulae (I), (II), (III), (IV) and (V) give general definitions of the azoles contained in the active compound combinations according to the invention.

Preferred azoles of formula (I) are those in which, $R^1$ represents a phenyl radical which is optionally monosubstituted, disubstituted or trisubstituted, the substituents being identical or different and being selected from fluorine, chlorine, bromine, phenyl, phenoxy, nitro alkyl having 1 to 4 carbon atoms, alkoxy having 1 to 4 carbon atoms, cycloalkyl having 3 to 7 carbon atoms, halogenoalkyl having 1 to 4 carbon atoms and 1 to 5 halogen atoms (particularly fluorine, chlorine and bromine atoms) and by cyano, $R^2$ represents a straight-chain or branched alkyl radical having 1 to 6 carbon atoms, or a halogenoalkyl radical having 1 to 6 carbon atoms and 1 to 5 halogen atoms (fluorine, chlorine and bromine being preferred), X represents oxygen or methylene, and Y represents carbonyl or a group —CH(OH).

The compounds listed in the following table may be individually mentioned as examples of azoles of the formula (I):

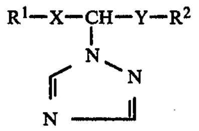

(I)

| $R^1$ | X | Y | $R^2$ |
|---|---|---|---|
| 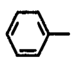 | O | CO | t-$C_4H_9$ |
| 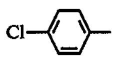 | O | CO | t-$C_4H_9$ |
| 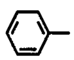 | O | CO | t-$C_4H_9$ |
| 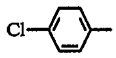 | O | CO | t-$C_4H_9$ |
| 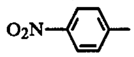 | $CH_2$ | CH(OH) | $—C(CH_3)_2CH_2F$ |
| 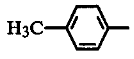 | $CH_2$ | CH(OH) | $—C(CH_3)_2CH_2F$ |
| 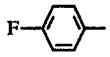 | $CH_2$ | CH(OH) | $—C(CH_3)_2CH_2F$ |
| 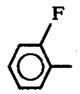 | $CH_2$ | CH(OH) | $—C(CH_3)_2CH_2F$ |
| 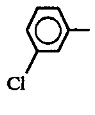 | $CH_2$ | CH(OH) | $—C(CH_3)_2CH_2F$ |

-continued

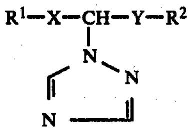

(I)

| $R^1$ | X | Y | $R^2$ |
|---|---|---|---|
| 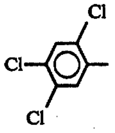 | $CH_2$ | CH(OH) | $-C(CH_3)_2CH_2F$ |
| 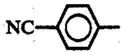 | $CH_2$ | CH(OH) | $-C(CH_3)_2CH_2F$ |
| 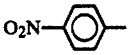 | $CH_2$ | CH(OH) | $-C(CH_3)_2CH_2Cl$ |
| 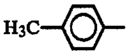 | $CH_2$ | CH(OH) | $-C(CH_3)_2CH_2Cl$ |
| 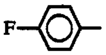 | $CH_2$ | CH(OH) | $-C(CH_3)_2CH_2Cl$ |
| 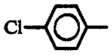 | $CH_2$ | CH(OH) | $-C(CH_3)_2CH_2Cl$ |
| 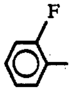 | $CH_2$ | CH(OH) | $-C(CH_3)_2CH_2Cl$ |
| 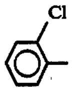 | $CH_2$ | CH(OH) | $-C(CH_3)_2CH_2Cl$ |
| 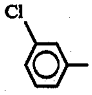 | $CH_2$ | CH(OH) | $-C(CH_3)_2CH_2Cl$ |
| 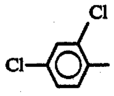 | $CH_2$ | CH(OH) | $-C(CH_3)_2CH_2Cl$ |
| 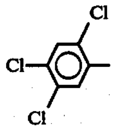 | $CH_2$ | CH(OH) | $-C(CH_3)_2CH_2Cl$ |
| 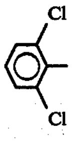 | $CH_2$ | CH(OH) | $-C(CH_3)_2CH_2Cl$ |
| 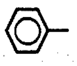 | $CH_2$ | CH(OH) | $-C(CH_3)_2CH_2Cl$ |
| 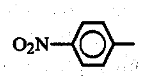 | $CH_2$ | CH(OH) | $-C(CH_2Cl)_2CH_3$ |
| 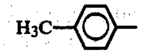 | $CH_2$ | CH(OH) | $-C(CH_2Cl)_2CH_3$ |

-continued

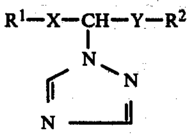

(I)

| $R^1$ | X | Y | $R^2$ |
|---|---|---|---|
| 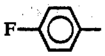 | $CH_2$ | CH(OH) | $-C(CH_2Cl)_2CH_3$ |
| 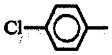 | $CH_2$ | CH(OH) | $-C(CH_2Cl)_2CH_3$ |
| 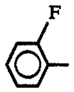 | $CH_2$ | CH(OH) | $-C(CH_2Cl)_2CH_3$ |
| 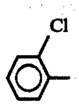 | $CH_2$ | CH(OH) | $-C(CH_2Cl)_2CH_3$ |
| 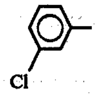 | $CH_2$ | CH(OH) | $-C(CH_2Cl)_2CH_3$ |
| 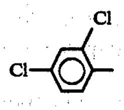 | $CH_2$ | CH(OH) | $-C(CH_2Cl)_2CH_3$ |
| 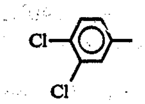 | $CH_2$ | CH(OH) | $-C(CH_2Cl)_2CH_3$ |
| 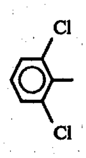 | $CH_2$ | CH(OH) | $-C(CH_2Cl)_2CH_3$ |
| 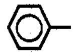 | $CH_2$ | CH(OH) | $-C(CH_2Cl)_2CH_3$ |
| 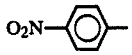 | $CH_2$ | CH(OH) | $-C(CH_2F)_2CH_3$ |
| 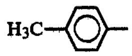 | $CH_2$ | CH(OH) | $-C(CH_2F)_2CH_3$ |
| 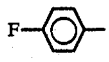 | $CH_2$ | CH(OH) | $C(CH_2F)_2CH_3$ |
| 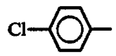 | $CH_2$ | CH(OH) | $C(CH_2F)_2CH_3$ |
| 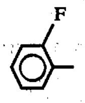 | $CH_2$ | CH(OH) | $C(CH_2F)_2CH_3$ |
| 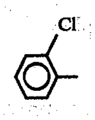 | $CH_2$ | CH(OH) | $C(CH_2F)_2CH_3$ |

-continued

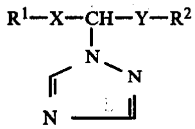

(I)

| $R^1$ | X | Y | $R^2$ |
|---|---|---|---|
| 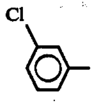 | $CH_2$ | CH(OH) | $C(CH_2F)_2CH_3$ |
| 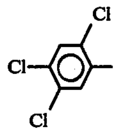 | $CH_2$ | CH(OH) | $C(CH_2F)_2CH_3$ |
| 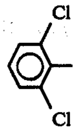 | $CH_2$ | CH(OH) | $C(CH_2F)_2CH_3$ |
| 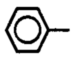 | $CH_2$ | CH(OH) | $C(CH_2F)_2CH_3$ |

Further particularly preferred azoles of the formula (I) are mentioned in the preparative examples hereinbelow.

Some of the azoles of the formula (I) are known (see DE-A (German Published Specification) No. 2,407,143 and DE-A (German Published Specification) No. 2,737,489).

Those azoles of the formula (I) in which $R^1$ represents an optionally substituted aryl radical, $R^2$ represents a tert.-butyl radical which is monosubstituted or disubstituted by halogen, X represents methylene and Y represents carbonyl or a group —CH(OH)—, are hitherto unknown. However, they can be prepared in a simple manner by reacting a triazolylmethyl-tert.-butyl ketone of the general formula

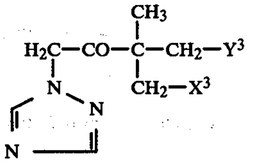

(IX)

in which $X^3$ represents a hydrogen or halogen atom and $Y^3$ represents a halogen atom, with a compound of the general formula $$R^{20}—Z^1 \quad (X)$$

in which $R^{20}$ represents an optionally substituted arylmethyl radical and $Z^1$ represents an electron-attracting leaving group (such as halogen, p-methylphenylsulphonyloxy or sulphate), in the usual manner in the presence of an inert organic solvent (such as dimethylsulphoxide) at a temperature between 0° C. and 100° C., and if appropriate, reducing the azole of the formula

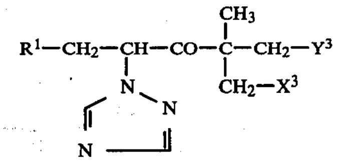

(Ia)

formed thereby, in which $R^1$, $X^3$ and Y have the meanings given above, according to known methods, in the presence of an inert diluent, at a temperature between 0° C. and 30° C. Complex hydrides (such as sodium borohydride, and lithium alanate) and also aluminum isopropylate or hydrogen in the presence of a catalyst are examples of suitable reducing agents.

Preferred azoles of formula (II) are those in which, $R^3$ represents an optionally monosubstituted or disubstituted, straight-chain or branched alkyl radical having 1 to 4 carbon atoms, preferred suitable substituents being selected from halogen, alkylcarbonyloxy having 1 to 4 carbon atoms in the alkyl part, alkylsulphonyloxy having 1 to 4 carbon atoms, and phenylsulphonyloxy which is optionally substituted by halogen or alkyl having 1 to 4 carbon atoms, or $R^3$ additionally represents a cycloalkyl radical having 5 to 7 carbon atoms, or an aryl radical which is optionally monosubstituted or polysubstituted by identical or different substituents and which has 6 to 10 carbon atoms (such as phenyl or naphthyl), preferred suitable substituents being selected from halogen, alkyl having 1 to 4 carbon atoms, phenyl, phenoxy, halogenophenyl and halogenophenoxy, $R^4$ represents a hydrogen atom or a straight-chain or branched alkyl radical having 1 to 4 carbon atoms, $R^5$ represents a hydrogen atom, a straight-chain or branched alkyl radical having 1 to 4 carbon atoms, a cycloalkyl radical having 5 to 7 carbon atoms, a cycloalkenyl radical which has 5 to 7 carbon atoms and is optionally substituted by alkyl having 1 to 4 carbon atoms, an alkenyl radical having 2 to 4 carbon atoms or an optionally substituted aryl radical having 6 to 10 carbon atoms (such as phenyl or naphthyl), halogen and alkyl having 1 to 4 carbon atoms being preferred suitable substituents, or in addition $R^4$ and $R^5$ together with the carbon atom to which they are bonded represent a cycloalkenyl radical which has 5 to 7 carbon atoms and which is optionally substituted by alkyl having 1 to 4 carbon atoms, or a cycloalkyl radical having 3 to 7 carbon atoms, $R^6$ represents a hydrogen atom or an alkyl radical having 1 to 4 carbon atoms, $X^1$ represents a group —$C(OR^7)R^8$—, or additionally represents a keto group if $R^3$ represents an optionally substituted alkyl or cycloalkyl radical, $R^7$ represents a hydrogen atom, a straight-chain or branched alkyl radical having 1 to 4 carbon atoms, an aralkyl radical which is optionally monosubstituted or polysubstituted by identical or different substituents and which has 1 or 2 carbon atoms in the alkyl part and 6 to 10 carbon atoms in the aryl part (such as benzyl or naphthylmethyl), preferred suitable substituents being selected from halogen, alkyl having 1 to 4 carbon atoms, halogenoalkyl having up to 2 carbon atoms and up to 3 identical or different halogen atoms (fluorine and chlorine being preferred), and optionally halogen-substituted phenyl and phenoxy, or $R^7$ represents an acyl radical —CO—$R^{21}$ or a carbamoyl radical —CO—$NR^{22}R^{23}$, wherein $R^{21}$ represents a straight-chain or branched alkyl radical having 1 to 4 carbon atoms, a halogenoalkyl radical having 1 or 2 carbon atoms and 1 to 5 identical or different halogen atoms (preferably fluorine and chlorine atoms) or an optionally substituted phenyl or benzyl radical, the preferred suitable substituents being selected from halogen and alkyl having 1 to 4 carbon atoms, $R^{22}$ represents a hydrogen atom or an alkyl radical having 1 to 4 carbon atoms, $R^{23}$ represents an alkyl radical having 1 to 8 carbon atoms, a halogenoalkyl radical having up to 4 carbon atoms and up to 5 identical or different halogen atoms (such as, in particular, fluorine and chlorine atoms), an aryl radical which is optionally monosubstituted or polysubstituted by identical or different substituents and which has 6 to 10 carbon atoms (such as phenyl and naphthyl) the preferred suitable substituents being selected from halogen, alkyl having 1 to 4 carbon atoms, and halogenoalkyl having up to 2 carbon atoms and up to 5 identical or different halogen atoms (such as, in particular, fluorine and chlorine atoms), or $R^{23}$ also represents a halogenoalkylmercapto radical having 1 or 2 carbon atoms and up to 5 halogen atoms (such as, in particular, fluorine and chlorine atoms), and $R^8$ represents a hydrogen atom, an alkyl radical having 1 to 4 carbon atoms or an aralkyl radical which has 1 or 2 carbon atoms in the alkyl part and 6 to 10 carbon atoms in the aryl part and which is optionally substituted by halogen or alkyl having 1 to 4 carbon atoms (such as, preferably, benzyl).

Those compounds of the formula (II) are very particularly preferred, in which $R^3$ represents a tert.-butyl, isopropyl, chloro-tert.-butyl, bromo-tert.-butyl, fluoro-tert.-butyl, acetoxy-tert.-butyl, methylsulphonyloxy-tert.-butyl, p-toluene-sulphonyloxy-tert.-butyl, 1,3-dichloro-2-methylprop-2-yl, 1,3-dibromo-2-methylprop-2-yl, 1,3-difluoro-2-methylprop-2-yl, 1-chloro-3-bromo-2-methylprop-2-yl, 1,3-diacetoxy-2-methylprop-2-yl, cyclohexyl, phenyl, chlorophenyl, bromophenyl, dichlorophenyl, fluorophenyl, methylphenyl, dimethylphenyl, chloromethylphenyl, biphenyl, phenoxyphenyl, chlorophenylphenyl or chlorophenoxyphenyl radical;

$R^4$ represents a hydrogen atom or a methyl, ethyl, propyl or butyl radical;

$R^5$ represents a hydrogen atom or a methyl, ethyl, isopropyl, cyclohexyl, cyclohexenyl, methylcyclohexenyl, allyl, methacryl, phenyl, chlorophenyl, dichlorophenyl or methylphenyl radical; or $R^4$ and $R^5$ together with the carbon atom to which they are bonded represent cyclopropyl, cyclobutyl, cyclopentyl, cyclohexyl, cyclohexenyl, or methylcyclohexenyl;

$R^6$ represents a hydrogen atom or a methyl, ethyl or n-propyl radical;

$X^1$ represents a group —C($OR^7$)$R^8$— or also represents a keto group if $R^3$, as optionally substituted alkyl or cycloalkyl, has the meanings already given immediately above;

$R^7$ represents a hydrogen atom or a methyl, ethyl, n-propyl, isopropyl or isobutyl radical, a naphthyl radical which is optionally substituted by chlorine, a benzyl radical which is optionally monosubstituted or polysubstituted, the substituents being identical or different, by a substituent selected from chlorine, fluorine, methyl, phenyl, chlorophenyl, phenoxy or chlorophenoxy, an acyl radical of the general formula —$COR^{21}$ or a carbamoyl radical of the general formula —CO—$NR^{22}R^{23}$; wherein $R^{21}$ represents a methyl, ethyl, isopropyl, isobutyl, chloromethyl or dichloromethyl radical or an optionally monosubstituted or polysubstituted phenyl or benzyl radical having chlorine, bromine or methyl as the substituents;

$R^{22}$ represents a hydrogen atom or a methyl or ethyl radical, and $R^{23}$ represents a methyl, ethyl, chloroethyl, phenyl, chlorophenyl, trifluoromethylmercapto, chlorodifluoromethylmercapto, dichlorofluoro-methylmercapto or trichloromethyl-mercapto radical, and $R^8$ represents a hydrogen atom or a methyl, ethyl, isopropyl, benzyl, chlorobenzyl, or dichlorobenzyl radical;

The compounds listed in the following table may be individually mentioned as examples of azoles of the formula (II).

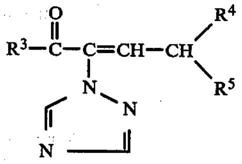

| $R^3$ | $R^4$ | $R^5$ |
|---|---|---|
| $C(CH_3)_3$ | $C_2H_5$ | $C_2H_5$ |
| $C(CH_3)_3$ | $C_2H_5$ | $CH_3$ |
| $C(CH_3)_3$ | $CH_3$ | $CH_3$ |
| $C(CH_3)_3$ | $CH_3$ | 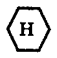 |
| $C(CH_3)_3$ | $CH_3$ | 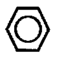 |
| $C(CH_3)_3$ | Cyclopropyl | |
| $C(CH_3)_3$ | Cyclobutyl | |
| $C(CH_3)_3$ | Cyclopentyl | |
| $C(CH_3)_3$ | Cycloheptyl | |
| $C(CH_3)_3$ | Norborn-3-en-2-yl | |
| 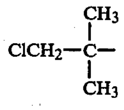 | Cyclohexane | |
| 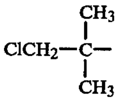 | Cyclohexene | |
| 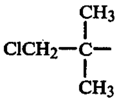 | Methylcyclohexene | |
| 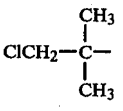 | $CH_3$ | $CH_3$ |

-continued

| | |
|---|---|
| 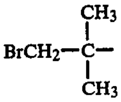 | Cyclohexane |
| 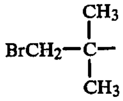 | Cyclohexene |
| 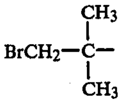 | Methylcyclohexene |
| 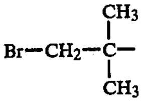 | Methylcyclohexene |
| 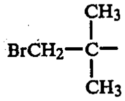 | CH3 CH3 |
| 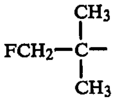 | Cyclohexane |
| 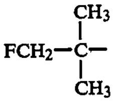 | Cyclohexene |
| 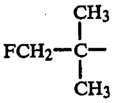 | Methylcyclohexene |
| 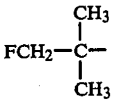 | CH3 CH3 |
| 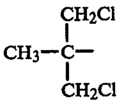 | Cyclohexane |
| 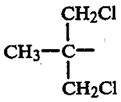 | Cyclohexene |
| 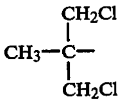 | Methylcyclohexene |
| 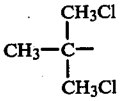 | CH3 CH3 |
| 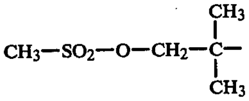 | Cyclohexane |

-continued

| | |
|---|---|
| 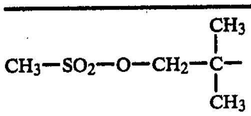 | Cyclohexene |
| 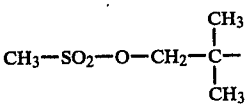 | Methylcyclohexene |
| 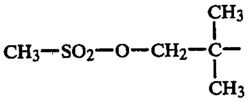 | CH3 CH3 |
| 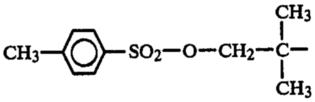 | Cyclohexane |
| 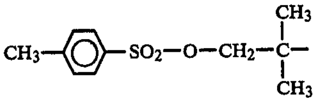 | Cyclohexene |
| 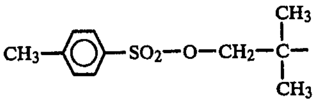 | Methylcyclohexene |
| 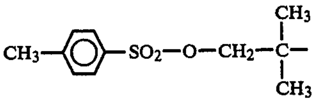 | CH3 CH3 |
| 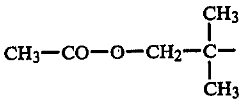 | Cyclohexane |
| 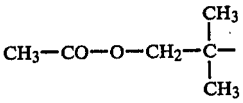 | Cyclohexene |
| 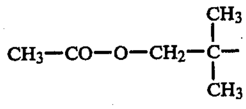 | Methylcyclohexene |
| 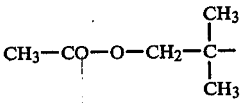 | CH3 CH3 |
| 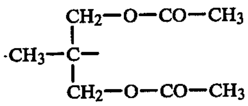 | Cyclohexane |
| 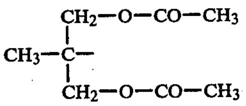 | Cyclohexene |
| 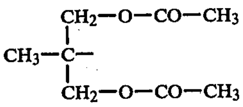 | Methylcyclohexene |

-continued

| | | |
|---|---|---|
| 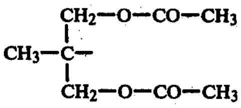 | CH3 | CH3 |
| 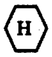 | Cyclohexane | |
| 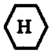 | Cyclohexene | |
| 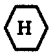 | Methylcyclohexene | |
| 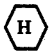 | CH3 | CH3 |

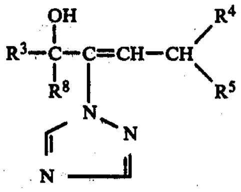

(IIb)

| R3 | R4 | R5 | R8 |
|---|---|---|---|
| C(CH3)3 | C2H5 | CH3 | H |
| C(CH3)3 | CH3 | CH3 | H |
| C(CH3)3 | CH3 | 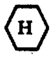 | H |
| C(CH3)3 | CH3 | 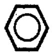 | H |
| C(CH3)3 | Cyclo-propyl | | H |
| C(CH3)3 | Cyclobutyl | | H |
| C(CH3)3 | Cyclo-pentyl | | H |
| C(CH3)3 | Cyclo-heptyl | | H |
| C(CH3)3 | CH3 | CH3 | CH3 |
| C(CH3)3 | Cyclo-hexane | | CH3 |
| C(CH3)3 | Cyclo-hexene | | CH3 |
| C(CH3)3 | Methyl-cyclo-hexene | | CH3 |
| C(CH3)3 | CH3 | CH3 | 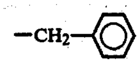 |
| C(CH3)3 | Cyclo-hexane | | 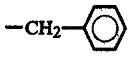 |
| C(CH3)3 | Cyclo-hexene | | 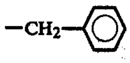 |
| C(CH3)3 | Methyl-cyclo-hexene | | 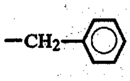 |
| 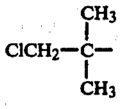 | CH3 | CH3 | H |

-continued

| | | | |
|---|---|---|---|
| 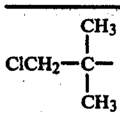 | Cyclo-hexane | | H |
| 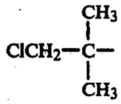 | Cyclo-hexene | | H |
| 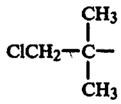 | Methyl-cyclo-hexene | | H |
| 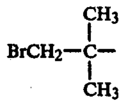 | CH3 | CH3 | H |
| 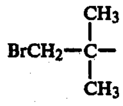 | Cyclo-hexane | | H |
| 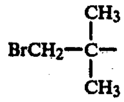 | Cyclo-hexene | | H |
| 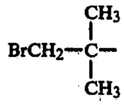 | Methyl-cyclo-hexene | | H |
| 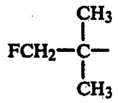 | CH3 | CH3 | H |
| 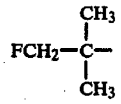 | Cyclo-hexane | | H |
| 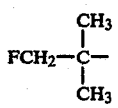 | Cyclo-hexene | | H |
| 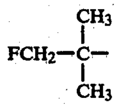 | Methyl-cyclo-hexene | | H |
| 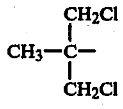 | CH3 | CH3 | H |
| 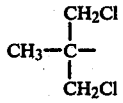 | Cyclo-hexane | | H |
| 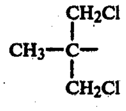 | Cyclo-hexene | | H |

-continued

| | | | |
|---|---|---|---|
| 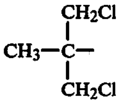 | Methyl-cyclo-hexene | | H |
| 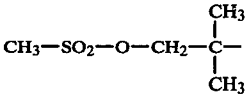 | CH3 | CH3 | H |
| 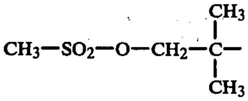 | Cyclo-hexane | | H |
| 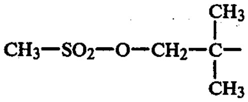 | Cyclo-hexene | | H |
| 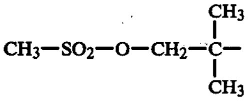 | Methyl-cyclo-hexene | | H |
| 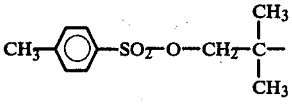 | CH3 | CH3 | H |
| 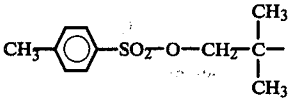 | Cyclo-hexane | | H |
| 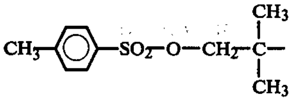 | Cyclo-hexene | | H |
| 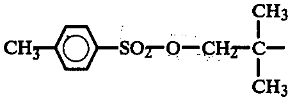 | Methyl-cyclo-hexene | | H |
| 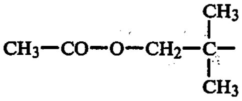 | CH3 | CH3 | H |
| 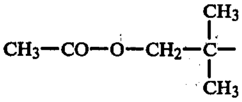 | Cyclo-hexane | | H |
| 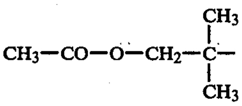 | Cyclo-hexene | | H |
| 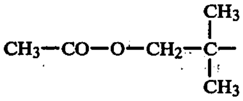 | Methyl-cyclo-hexene | | H |
| 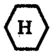 | CH3 | CH3 | H |
| 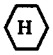 | Cyclo-hexane | | H |

-continued

| | | | |
|---|---|---|---|
| 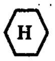 | Cyclo-hexene | | H |
| 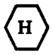 | Methyl-cyclo-hexene | | H |
| 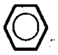 | CH3 | CH3 | H |
| 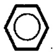 | Cyclo-hexane | | H |
| 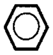 | Cyclo-hexene | | H |
| 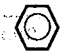 | Methyl-cyclo-hexene | | H |
| 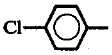 | CH3 | CH3 | H |
| 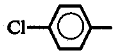 | Cyclo-hexane | | H |
| 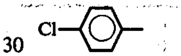 | Cyclo-hexene | | H |
| 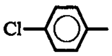 | Methyl-cyclo-hexene | | H |
| 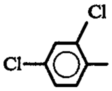 | CH3 | CH3 | H |
| 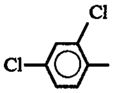 | Cyclo-hexane | | H |
| 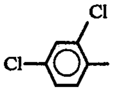 | Cyclo-hexene | | H |
| 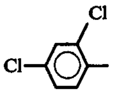 | Methyl-cyclo-hexene | | H |

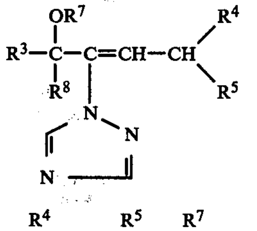 (IIc)

| $R^3$ | $R^4$ | $R^5$ | $R^7$ | $R^8$ |
|---|---|---|---|---|
| $C(CH_3)_3$ | $CH_3$ | $CH_3$ | $C_2H_5$ | H |
| $C(CH_3)_3$ | Cyclohexane | | $C_2H_5$ | H |
| $C(CH_3)_3$ | Cyclohexene | | $C_2H_5$ | H |
| $C(CH_3)_4$ | Methylcyclohexene | | $C_2H_5$ | H |
| 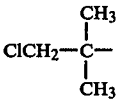 | $CH_3$ | $CH_3$ | $C_2H_5$ | $CH_3$ |

-continued

| | | | | |
|---|---|---|---|---|
| 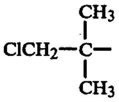 | Cyclohexane | | $C_2H_5$ | $CH_3$ |
| 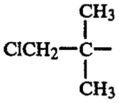 | Cyclohexene | | $C_2H_5$ | $CH_3$ |
| 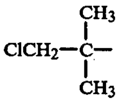 | Methylcyclohexene | | $C_2H_5$ | $CH_3$ |
| 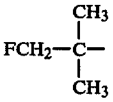 | $CH_3$ | $CH_3$ | $C_2H_5$ | H |
| 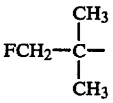 | Cyclohexane | | $C_2H_5$ | H |
| 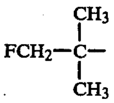 | Cyclohexene | | $C_2H_5$ | H |
| 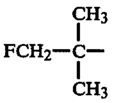 | Methylcyclohexene | | $C_2H_5$ | H |
| 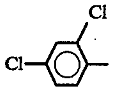 | $CH_3$ | $CH_3$ | $C_2H_5$ | H |
| 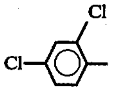 | Cyclohexane | | $C_2H_5$ | H |
| 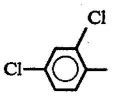 | Cyclohexane | | $C_2H_5$ | H |
| 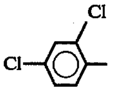 | Methylcyclohexene | | $C_2H_5$ | H |
| $C(CH_3)_3$ | $CH_3$ | $CH_3$ | 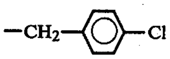 | H |
| $C(CH_3)_3$ | Cyclohexane | | 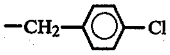 | H |
| $C(CH_3)_3$ | Cyclohexene | | 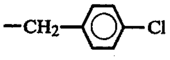 | H |
| $C(CH_3)_3$ | Methylcyclohexene | | 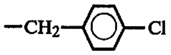 | H |
| 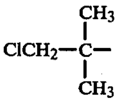 | $CH_3$ | $CH_3$ | 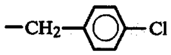 | H |

-continued

| | | | | |
|---|---|---|---|---|
| 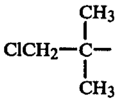 | Cyclohexane | | 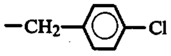 | H |
| 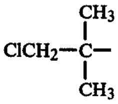 | Cyclohexene | | 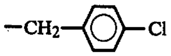 | H |
| 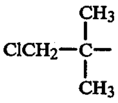 | Methylcyclohexene | | 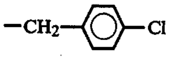 | H |
| 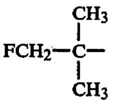 | $CH_3$ | $CH_3$ | 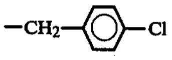 | H |
| 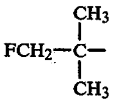 | Cyclohexane | | 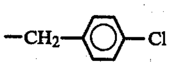 | H |
| 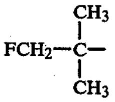 | Cyclohexene | | 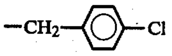 | H |
| 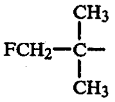 | Methylcyclohexene | | 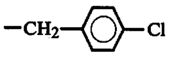 | H |
| 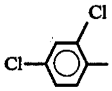 | $CH_3$ | $CH_3$ | 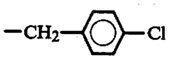 | H |
| 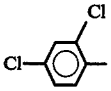 | Cyclohexane | | 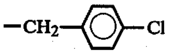 | H |
| 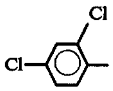 | Cyclohexene | | 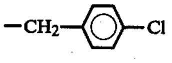 | H |
| 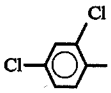 | Methylcyclohexene | | 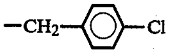 | H |
| 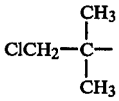 | $CH_3$ | $CH_3$ | $-CO-CH_3$ | H |
| | Cyclohexane | | $-CO-CH_3$ | H |
| | Cyclohexene | | $-CO-CH_3$ | H |
| | Methylcyclohexene | | $-CO-CH_3$ | H |

-continued

| | | | | |
|---|---|---|---|---|
| 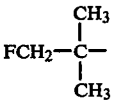 | $CH_3$ | $CH_3$ | $-CO-CH_3$ | H |
| 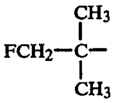 | Cyclohexane | | $-CO-CH_3$ | H |
| 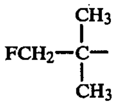 | Cyclohexene | | $-CO-CH_3$ | H |
| 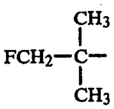 | Methylcyclohexene | | $-CO-CH_3$ | H |
| 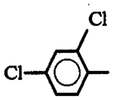 | $CH_3$ | $CH_3$ | $-CO-CH_3$ | H |
| 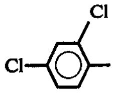 | Cyclohexane | | $-CO-CH_3$ | H |
| 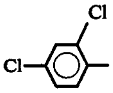 | Cyclohexene | | $-CO-CH_3$ | H |
| 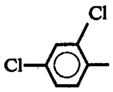 | Methylcyclohexene | | $-CO-CH_3$ | H |
| 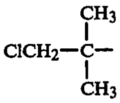 | $CH_3$ | $CH_3$ | $-CO-NHCH_3$ | H |
| 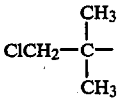 | Cyclohexane | | $-CO-NHCH_3$ | H |
| 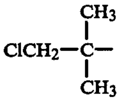 | Cyclohexene | | $-CO-NHCH_3$ | H |
| 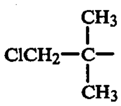 | Methylcyclohexene | | $-CO-NHCH_3$ | H |
| 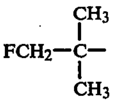 | $CH_3$ | $CH_3$ | $-CO-NHCH_3$ | H |
| 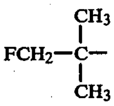 | Cyclohexane | | $-CO-NHCH_3$ | H |

-continued

| | | | | |
|---|---|---|---|---|
| 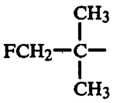 | Cyclohexene | | $-CO-NHCH_3$ | H |
| 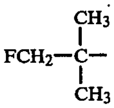 | Methylcyclohexene | | $-CO-NHCH_3$ | H |
| 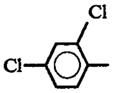 | $CH_3$ | $CH_3$ | $-CO-NHCH_3$ | H |
| 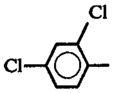 | Cyclohexane | | $-CO-NHCH_3$ | H |
| 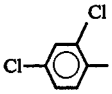 | Cyclohexene | | $-CO-NHCH_3$ | H |
| 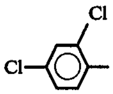 | Methylcyclohexene | | $-CO-NHCH_3$ | H |
| 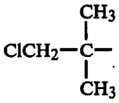 | $CH_3$ | $CH_3$ | 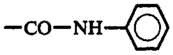 | H |
| 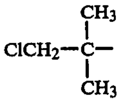 | Cyclohexane | | 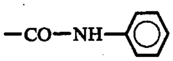 | H |
| 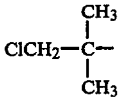 | Cyclohexene | | 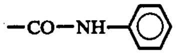 | H |
| 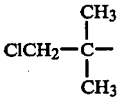 | Methylcyclohexene | | 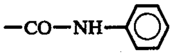 | H |
| 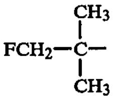 | $CH_3$ | $CH_3$ | 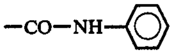 | H |
| 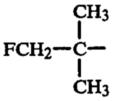 | Cyclohexane | | 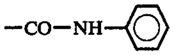 | H |
| 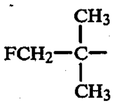 | Cyclohexene | | 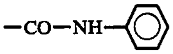 | H |
| 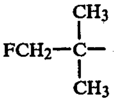 | Methylcyclohexene | | 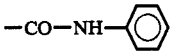 | H |
| 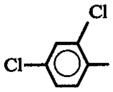 | $CH_3$ | $CH_3$ | 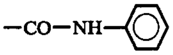 | H |

-continued

| | | | | |
|---|---|---|---|---|
| 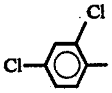 | Cyclohexane | | 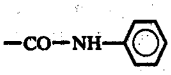 | H |
| 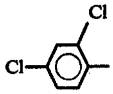 | Cyclohexene | | 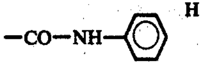 | H |
| 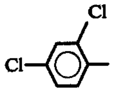 | Methylcyclohexene | | 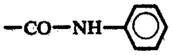 | H |
| 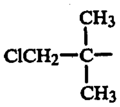 | $CH_3$ | $CH_3$ | 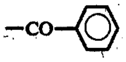 | H |
| 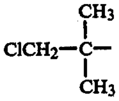 | Cyclohexane | | 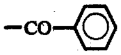 | H |
| 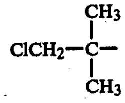 | Cyclohexane | | 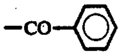 | H |
| 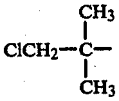 | Methylcyclohexene | | 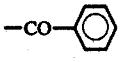 | H |
| 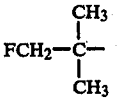 | $CH_3$ | $CH_3$ | 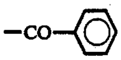 | H |
| | Cyclohexane | | 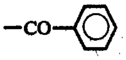 | H |
| | Cyclohexene | | 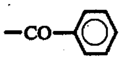 | H |
| | Methylcyclohexene | | 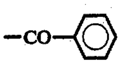 | H |
| 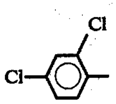 | $CH_3$ | $CH_3$ | 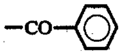 | H |
| 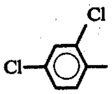 | Cyclohexane | | 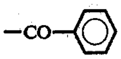 | H |
| 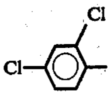 | Cyclohexene | | 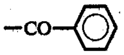 | H |
| 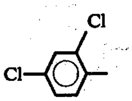 | Methylcyclohexene | | 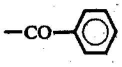 | H |
| 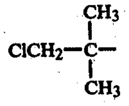 | $CH_3$ | $CH_3$ | $-CO-CHCl_2$ | H |
| 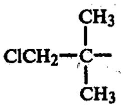 | Cyclohexane | | $-CO-CHCl_2$ | H |
| 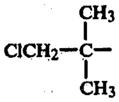 | Cyclohexene | | $-CO-CHCl_2$ | H |
| 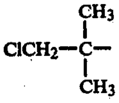 | Methylcyclohexene | | $-CO-CHCl_2$ | H |
| 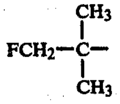 | $CH_3$ | $CH_3$ | $-CO-CHCl_2$ | H |
| 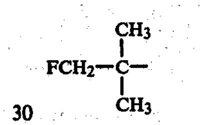 | Cyclohexane | | $-CO-CHCl_2$ | H |
| 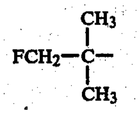 | Cyclohexene | | $-CO-CHCl_2$ | H |
| 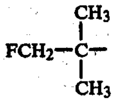 | Methylcyclohexene | | $-CO-CHCl_2$ | H |
| 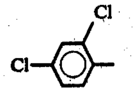 | $CH_3$ | $CH_3$ | $-CO-CHCl_2$ | H |
| 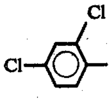 | Cyclohexane | | $-CO-CHCl_2$ | H |
| 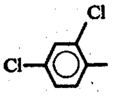 | Cyclohexene | | $-CO-CHCl_2$ | H |
| 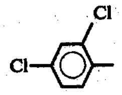 | Methylcyclohexene | | $-CO-CHCl_2$ | H |
| $C(CH_3)_3$ | $CH_3$ | $CH_3$ | $-CO-CH_3$ | H |
| $C(CH_3)_3$ | Cyclohexane | | $-CO-CH_3$ | H |
| $C(CH_3)_3$ | Cyclohexene | | $-CO-CH_3$ | H |
| $C(CH_3)_3$ | Methylcyclohexene | | $-CO-CH_3$ | H |
| $C(CH_3)_3$ | $CH_3$ | $CH_3$ | $-CO-NHCH_3$ | H |
| $C(CH_3)_3$ | Cyclohexane | | $-CO-NHCH_3$ | H |
| $C(CH_3)_3$ | Cyclohexene | | $-CO-NHCH_3$ | H |
| $C(CH_3)_3$ | Methylcyclohexene | | $-CO-NHCH_3$ | H |
| $C(CH_3)_3$ | $CH_3$ | $CH_3$ | 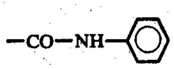 | H |

-continued

| | | | |
|---|---|---|---|
| $C(CH_3)_3$ | Cyclohexane | 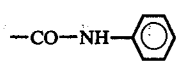 | H |
| $C(CH_3)_3$ | Cyclohexene | 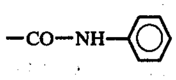 | H |
| $C(CH_3)_3$ | Methylcyclohexene | 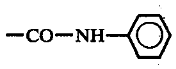 | H |
| $C(CH_3)_3$ | $CH_3$ $CH_3$ | 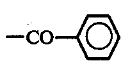 | H |
| $C(CH_3)_3$ | Cyclohexane | 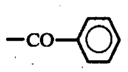 | H |
| $C(CH_3)_3$ | Cyclohexane | 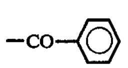 | H |
| $C(CH_3)_3$ | Methylcyclohexene | 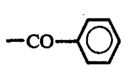 | H |
| $C(CH_3)_3$ | $CH_3$ $CH_3$ | $-CO-CHCl_2$ | H |
| $C(CH_3)_3$ | Cyclohexane | $-CO-CHCl_2$ | H |
| $C(CH_3)_3$ | Cyclohexene | $-CO-CHCl_2$ | H |
| $C(CH_3)_3$ | Methylcyclohexene | $-CO-CHCl_2$ | H |

Further particularly preferred azoles of the formula (II) are mentioned in the Preparative Examples.

The azoles of the formula (II) are already known (see U.S. Application Ser. No. 152,949 filed May 23, 1980, now pending and DE-A (German Published Specification) No. 2,645,617).

The compounds of the formula (II) can be present in two geometric isomer forms, according to the arrangement of the groups which are bonded to the double bond. If $X^1$ represents the group $-C(OR^7)R^8-$, an asymmetric carbon atom is present, so that the compounds of the formula (II) may additionally be present in two optical isomer forms. The present invention relates to compositions comprising the individual isomers as well as compositions comprising the isomer mixtures.

Preferred azoles of formula (III) are those in which, $R^9$ represents a phenyl radical which is optionally monosubstituted, disubstituted or trisubstituted, the substituents being identical or different, and being selected from fluorine, chlorine, bromine, phenyl, phenoxy, nitro, alkyl having 1 to 4 carbon atoms, alkoxy having 1 to 4 carbon atoms, cycloalkyl having 3 to 7 carbon atoms, halogenoalkyl having 1 to 4 carbon atoms and 1 to 5 halogen atoms (particularly fluorine, chlorine and bromine atoms) and cyano, $R^{10}$ represents a straight-chain or branched alkyl radical having 1 to 6 carbon atoms, a halogenoalkyl radical having 1 to 6 carbon atoms, and 1 to 5 halogen atoms (fluorine, chlorine and bromine being preferred), a phenyl radical which is optionally monosubstituted, disubstituted or trisubstituted, the substituents being identical or different, and being selected from fluorine, chlorine, bromine, phenyl, phenoxy, nitro, alkyl having 1 to 4 carbon atoms, alkoxy having 1 to 4 carbon atoms, cycloalkyl having 3 to 7 carbon atoms, halogenoalkyl having 1 to 4 carbon atoms and 1 to 5 halogen atoms (particularly fluorine, chlorine and bromine atoms) and cyano, and $Y^1$ represents a carbonyl group or a group $-CH(OH)-$.

The compounds listed in the following table may be individually mentioned as examples of azoles of the formula (III):

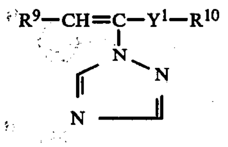

(III)

| $R^9$ | $Y^1$ | $R^{10}$ |
|---|---|---|
| 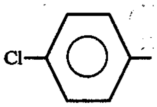 | CH(OH) | tert.-$C_4H_9$ |
| 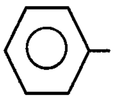 | CH(OH) | tert.-$C_4H_9$ |
| 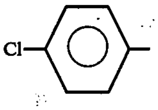 | CH(OH) | $-C(CH_3)_2CH_2Cl$ |
| 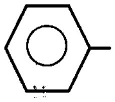 | CO | tert.-$C_4H_9$ |
| 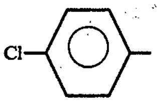 | CO | tert.-$C_4H_9$ |
| 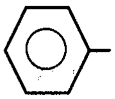 | CO | $-C(CH_3)_2CH_2Cl$ |
| 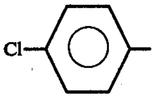 | CO | $-C(CH_3)_2CH_2Cl$ |
| 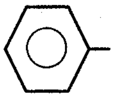 | CO | 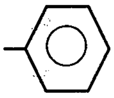 |
| 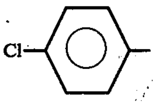 | CO | 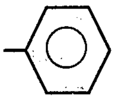 |
| 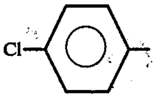 | CO | 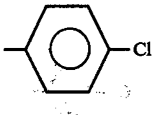 |
| 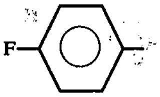 | CO | 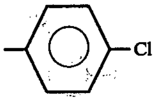 |

-continued
| $R^9$ | $Y^1$ | $R^{10}$ |
| --- | --- | --- |
| 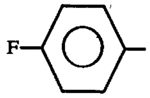 | CO | 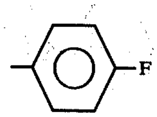 |
| 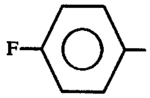 | CO | 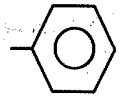 |
| 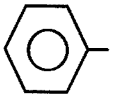 | CO | $-CH_3$ |
| 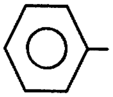 | CO | $-C_2H_5$ |
| 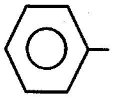 | CO | $-C_3H_7-$n |
| 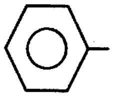 | CO | $-C_3H_7-$iso |
| 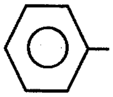 | CH(OH) | tert.-$C_4H_9$ |
| 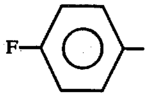 | CH(OH) | tert.-$C_4H_9$ |
| 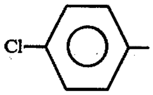 | CH(OH) | tert.-$C_4H_9$ |
| 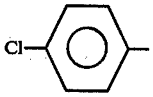 | CO | $-C(CH_2Cl)_2CH_3$ |
| 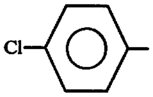 | CH(OH) | $-C(CH_2Cl)_2CH_3$ |
| 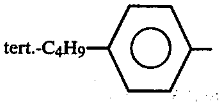 | CO | $-C(CH_2Cl)_2CH_3$ |
| 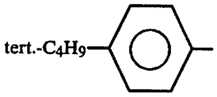 | CH(OH) | $-C(CH_2Cl)_2CH_3$ |
-continued
| $R^9$ | $Y^1$ | $R^{10}$ |
| --- | --- | --- |
| 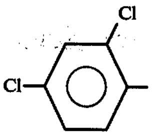 | CO | $-C(CH_2Cl)_2CH_3$ |
| 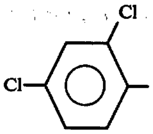 | CH(OH) | $-C(CH_2Cl)_2CH_3$ |
| 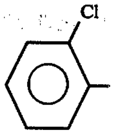 | CO | $-C(CH_2Cl)_2CH_3$ |
| 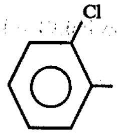 | CH(OH) | $-C(CH_2Cl)_2CH_3$ |
| 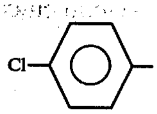 | CO | $-C(CH_2F)_2CH_3$ |
| 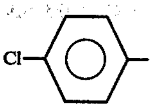 | CH(OH) | $-C(CH_2F)_2CH_3$ |
| 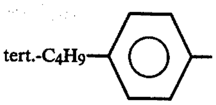 | CO | $-C(CH_2F)_2CH_3$ |
| 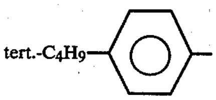 | CH(OH) | $-C(CH_2F)_2CH_3$ |
| 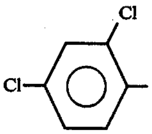 | CO | $-C(CH_2F)_2CH_3$ |
| 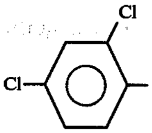 | CH(OH) | $-C(CH_2F)_2CH_3$ |
| 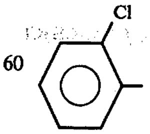 | CO | $-C(CH_2F)_2CH_3$ |
| 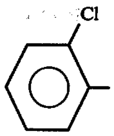 | CH(OH) | $-C(CH_2F)_2CH_3$ |

-continued

| $R^9$ | $Y^1$ | $R^{10}$ |
|---|---|---|
| 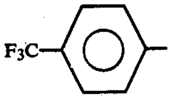 | CO | $-C(CH_3)_2CH_2Cl$ |
| 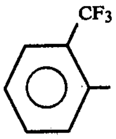 | CO | $-C(CH_3)_2CH_2Cl$ |
| 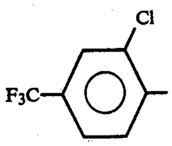 | CO | $-C(CH_3)_2CH_2Cl$ |
| 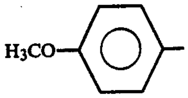 | CO | $-C(CH_3)_2CH_2Cl$ |
| 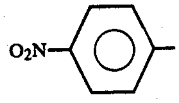 | CO | $-C(CH_3)_2CH_2Cl$ |
| 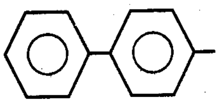 | CO | $-C(CH_3)_2CH_2Cl$ |
| 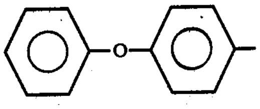 | CO | $-C(CH_3)_2CH_2Cl$ |
| 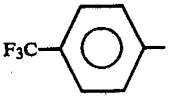 | CH(OH) | $-C(CH_3)_2CH_2Cl$ |
| 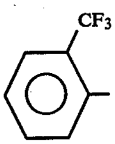 | CH(OH) | $-C(CH_3)_2CH_2Cl$ |
| 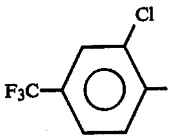 | CH(OH) | $-C(CH_3)_2CH_2Cl$ |
| 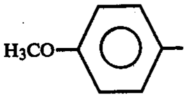 | CH(OH) | $-C(CH_3)_2CH_2Cl$ |
| 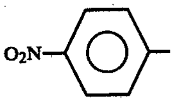 | CH(OH) | $-C(CH_3)_2CH_2Cl$ |

-continued

| $R^9$ | $Y^1$ | $R^{10}$ |
|---|---|---|
| 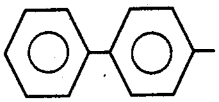 | CH(OH) | $-C(CH_3)_2CH_2Cl$ |
| 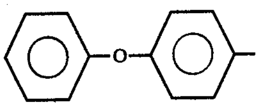 | CH(OH) | $-C(CH_3)_2CH_2Cl$ |
| 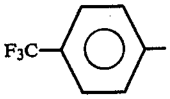 | CO | $-C(CH_3)_2CH_2F$ |
| 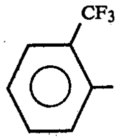 | CO | $-C(CH_3)_2CH_2F$ |
| 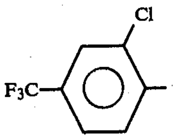 | CO | $-C(CH_3)_2CH_2F$ |
| 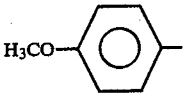 | CO | $-C(CH_3)_2CH_2F$ |
| 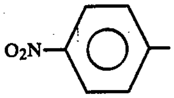 | CO | $-C(CH_3)_2CH_2F$ |
| 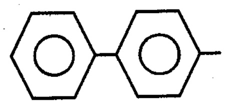 | CO | $-C(CH_3)_2CH_2F$ |
| 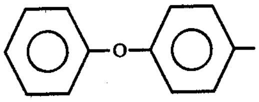 | CO | $-C(CH_3)_2CH_2F$ |
| 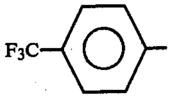 | CH(OH) | $-C(CH_3)_2CH_2F$ |
| 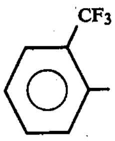 | CH(OH) | $-C(CH_3)_2CH_2F$ |
| 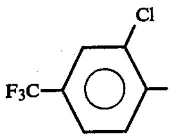 | CH(OH) | $-C(CH_3)_2CH_2F$ |

-continued

| $R^9$ | $Y^1$ | $R^{10}$ |
|---|---|---|
| 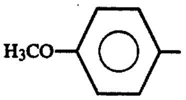 | CH(OH) | $-C(CH_3)_2CH_2F$ |
| 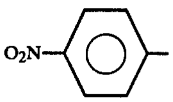 | CH(OH) | $-C(CH_3)_2CH_2F$ |
| 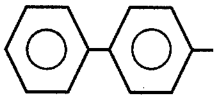 | CH(OH) | $-C(CH_3)_2CH_2F$ |
| 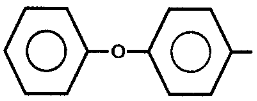 | CH(OH) | $-C(CH_3)_2CH_2F$ |

Further particularly preferred azoles of the formula (III) are mentioned in the preparative examples hereinbelow.

Some of the azoles of the formula (III) are known (see DE-A (German Published Specification) No. 2,645,617, DE-A (German Published Specification) No. 2,838,847, JP-A (Japanese Published Specification) No. 53,130,661 and U.S. application Ser. No. 144,110, filed Apr. 28, 1980, now pending.

The azoles of the formula (III) can be present in two geometric isomer forms, according to the arrangement of the groups which are bonded to the double bond. If $Y^1$ represents the group —CH(OH)—, an asymmetric carbon atom is present, so that the compounds of the formula (III) can also be present in this case in two optical isomer forms. The present invention relates to compositions comprising the individual isomers as well as compositions comprising the isomer mixtures.

Those azoles of the formula (III) in which $R^9$ represents an optionally substituted aryl radical, $R^{10}$ represents a tert.-butyl radical which is monosubstituted or disubstituted by halogen, and $Y^1$ represents a carbonyl group or a group —CH(OH)—, are hitherto unknown. However, they can be prepared in a simple manner by reacting a triazolylmethyl-tert.-butyl ketone of the general formula

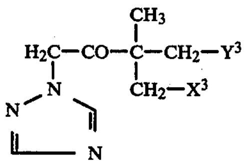

(IX)

in which $X^3$ and $Y^3$ have the meanings given above, with an aldehyde of the general formula $$R^9—CH=O \quad (XI)$$

in which $R^9$ has the meaning given above, in the presence of an inert organic solvent and in the presence of a catalyst (such as a mixture of piperidine and glacial acetic acid) at a temperature between 20° C. and 160° C., and, if appropriate, reducing the azole of the general formula

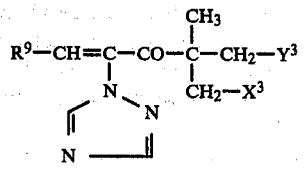

(IIIa)

formed thereby, in which, $R^9$, $X^3$ and $Y^3$ have the meanings given above, according to known methods, in the presence of an inert diluent at a temperature between 0° C. and 30° C. Complex hydrides (such as sodium borohydride and lithium alanate) and also aluminum isopropylate or hydrogen in the presence of a catalyst are examples of suitable reducing agents.

Preferred azoles of formula (IV) are those in which, $R^{11}$ and $R^{12}$ are identical or different and represent a cycloalkyl radical which is optionally substituted by methyl and which has 5 or 6 carbon atoms, a straight-chain or branched alkyl radical having 1 to 4 carbon atoms, a halogenoalkyl radical having 1 to 4 carbon atoms and 1 to 5 halogen atoms (such as fluorine or chlorine) or a phenyl radical which is optionally substituted by substituent(s) selected from fluorine, chlorine, bromine, alkyl having 1 to 4 carbon atoms, alkoxy having 1 to 4 carbon atoms, phenyl and nitro.

The azoles of the formula (IV) are known (see EP-A (European Published Patent Application) No. 0,005,600).

Preferred azoles of formula (V), are those in which, $R^{13}$ represents a straight-chain or branched alkyl radical having 1 to 4 carbon atoms, a cycloalkyl radical which has 3 to 7 carbon atoms and which is optionally substituted by alkyl having 1 or 2 carbon atoms, or a phenyl radical which is optionally monosubstituted or polysubstituted by identical or different substituents, preferred suitable substituents being selected from halogen, alkyl having 1 to 4 carbon atoms and halogenoalkyl having 1 to 2 carbon atoms and 1 to 5 identical or different halogen atoms (such as, in particular, fluorine and chlorine atoms), Z represents a halogen atom, a straight-chain or branched alkyl radical having 1 to 4 carbon atoms, a cycloalkyl radical having 5 to 7 carbon atoms, an alkoxy and alkylthio radical, each having 1 to 4 carbon atoms, a halogenoalkyl, halogenoalkoxy or halogenoalkylthio radical each having 1 or 2 carbon atoms and 1 to 5 identical or different halogen atoms (such as, in particular, fluorine and chlorine atoms), or an optionally halogen- and/or $C_{1-4}$-alkyl-substituted phenyl, phenoxy, phenylalkyl or phenyl-alkoxy radical having 1 or 2 carbon atoms in the alkyl or alkoxy part, and $X^2$, $Y^2$ and m have the meanings given above.

Particularly preferred azoles of formula (VI) are those in which $R^{13}$ represents a tert.-butyl, isopropyl or methyl radical, a cyclopropyl, cyclopentyl or cyclohexyl radical, which is optionally substituted by methyl in each case, or a phenyl radical which is optionally monosubstituted or disubstituted, the substituents being identical or different and being selected from fluorine, chlorine, methyl and trifluoromethyl;

Z represents a fluorine, chlorine or bromine atom, a methyl, tert.-butyl, cyclohexyl, methoxy, methylthio, trifluoromethyl, trifluoromethoxy or trifluoromethylthio radical or a phenyl, phenoxy, benzyl or benzyloxy radical which is in each case optionally monosubstituted or disubstituted, the substituents being identical or different and being selected from fluorine, chlorine and methyl, and $X^2$, $Y^2$ and m have the meaning given above.

The compounds listed in the following table may be individually mentioned as examples of azole of the formula (V):

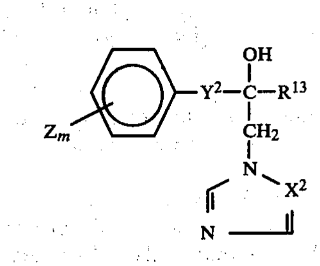

| $Z_m$ | $Y^2$ | $R^{13}$ | $X^2$ |
|---|---|---|---|
| 4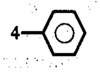 | $-O-CH_2-$ | $-C(CH_3)_3$ | N(CH) |
| 4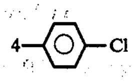 | " | " | " |
| 4-O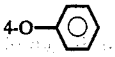 | " | " | " |
| 4-O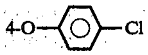 | " | " | " |
| 4-$CH_2$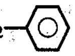 | " | " | " |
| 4-$CH_2$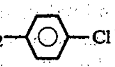 | " | " | " |
| 4-O-$CH_2$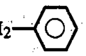 | " | " | " |
| 4-O-$CH_2$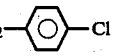 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4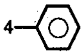 | $-O-CH_2$ | 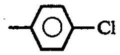 | " |
| 4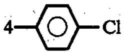 | " | " | " |
| 4-O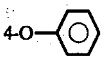 | " | " | " |

-continued

| $Z_m$ | $Y^2$ | $R^{13}$ | $X^2$ |
|---|---|---|---|
| 4-O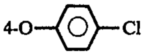 | " | " | " |
| 4-$CH_2$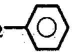 | " | " | " |
| 4-$CH_2$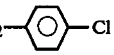 | " | " | " |
| 4-O-$CH_2$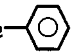 | " | " | " |
| 4-O-$CH_2$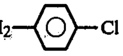 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4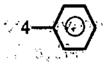 | $-O-CH_2-$ | $-CH(CH_3)_2$ | " |
| 4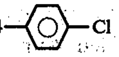 | " | " | " |
| 4-O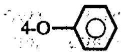 | " | " | " |
| 4-O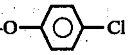 | " | " | " |
| 4-$CH_2$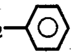 | " | " | " |
| 4-$CH_2$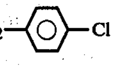 | " | " | " |
| 4-O-$CH_2$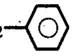 | " | " | " |
| 4-O-$CH_2$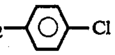 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4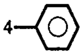 | " | 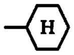 | " |
| 4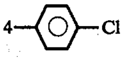 | " | " | " |
| 4-O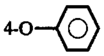 | " | " | " |
| 4-O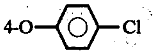 | " | " | " |

-continued

| $Z_m$ | $Y^2$ | $R^{13}$ | $X^2$ |
|---|---|---|---|
| 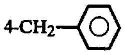 | " | " | " |
| 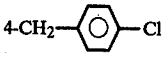 | " | " | " |
| 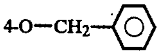 | " | " | " |
| 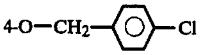 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 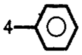 | " | 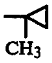 | " |
| 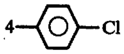 | " | " | " |
| 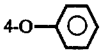 | " | " | " |
| 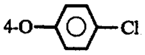 | " | " | " |
| 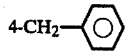 | " | " | " |
| 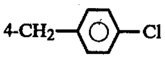 | " | " | " |
| 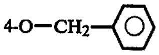 | " | " | " |
| 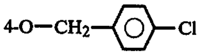 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 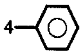 | $—CH_2—CH_2—$ | $—C(CH_3)_3$ | " |
| 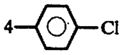 | " | " | " |
| 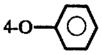 | " | " | " |
| 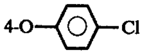 | " | " | " |

-continued

| $Z_m$ | $Y^2$ | $R^{13}$ | $X^2$ |
|---|---|---|---|
| 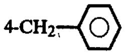 | " | " | " |
| 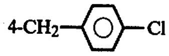 | " | " | " |
| 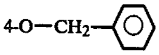 | " | " | " |
| 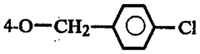 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 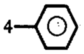 | " | 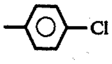 | " |
| 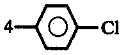 | " | " | " |
| 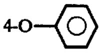 | " | " | " |
| 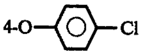 | " | " | " |
| 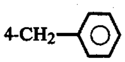 | " | " | " |
| 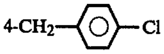 | " | " | " |
| 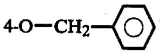 | " | " | " |
| 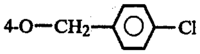 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 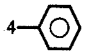 | " | $—CH(CH_3)_2$ | " |
| 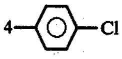 | " | " | " |
| 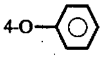 | " | " | " |
| 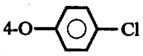 | " | " | " |
| 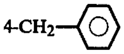 | " | " | " |

-continued

| $Z_m$ | $Y^2$ | $R^{13}$ | $X^2$ |
|---|---|---|---|
| 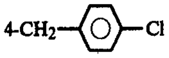 | " | " | " |
| 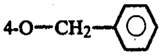 | " | " | " |
| 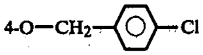 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 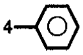 | " | 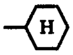 | " |
| 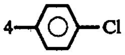 | " | " | " |
| 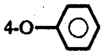 | " | " | " |
| 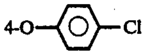 | " | " | " |
| 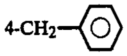 | " | " | " |
| 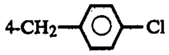 | " | " | " |
| 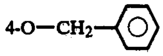 | " | " | " |
| 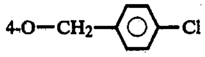 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 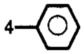 | " | 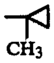 | " |
| 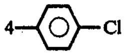 | " | " | " |
| 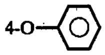 | " | " | " |
| 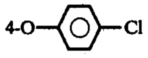 | " | " | " |
| 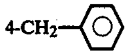 | " | " | " |

-continued

| $Z_m$ | $Y^2$ | $R^{13}$ | $X^2$ |
|---|---|---|---|
| 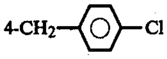 | " | " | " |
| 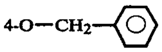 | " | " | " |
| 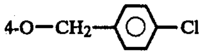 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 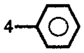 | $-CH{=}CH-$ | $-C(CH_3)_3$ | " |
| 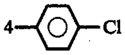 | " | " | " |
| 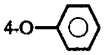 | " | " | " |
| 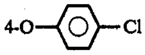 | " | " | " |
| 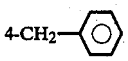 | " | " | " |
| 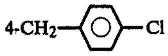 | " | " | " |
| 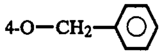 | " | " | " |
| 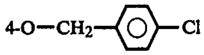 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 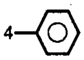 | " | 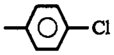 | " |
| 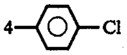 | " | " | " |
| 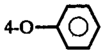 | " | " | " |
| 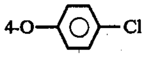 | " | " | " |
| 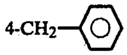 | " | " | " |
| 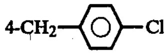 | " | " | " |

-continued

| $Z_m$ | $Y^2$ | $R^{13}$ | $X^2$ |
|---|---|---|---|
| 4-O—$CH_2$— 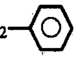 | " | " | " |
| 4-O—$CH_2$— 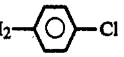 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4— 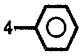 | " | —$CH(CH_3)_2$ | " |
| 4— 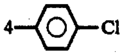 | " | " | " |
| 4-O— 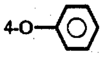 | " | " | " |
| 4-O— 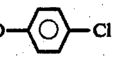 | " | " | " |
| 4-$CH_2$— 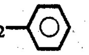 | " | " | " |
| 4-$CH_2$— 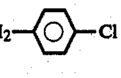 | " | " | " |
| 4-O—$CH_2$— 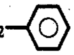 | " | " | " |
| 4-O—$CH_2$— 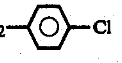 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4— 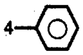 | " | 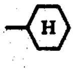 | " |
| 4— 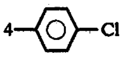 | " | " | " |
| 4-O— 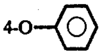 | " | " | " |
| 4-O— 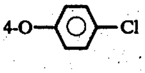 | " | " | " |
| 4-$CH_2$— 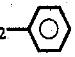 | " | " | " |
| 4-$CH_2$— 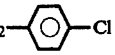 | " | " | " |

-continued

| $Z_m$ | $Y^2$ | $R^{13}$ | $X^2$ |
|---|---|---|---|
| 4-O—$CH_2$— 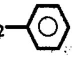 | " | " | " |
| 4-O—$CH_2$— 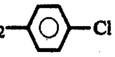 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4— 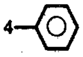 | " | 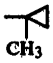 | " |
| 4— 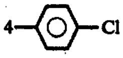 | " | " | " |
| 4-O— 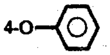 | " | " | " |
| 4-O— 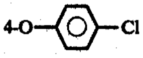 | " | " | " |
| 4-$CH_2$— 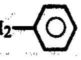 | " | " | " |
| 4-$CH_2$— 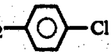 | " | " | " |
| 4-O—$CH_2$— 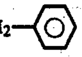 | " | " | " |
| 4-O—$CH_2$— 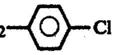 | " | " | " |
| 3,4-$Cl_2$ | " | " | " |
| 4-$CF_3$ | " | " | " |
| 4-$OCF_3$ | " | " | " |
| 4-$SCF_3$ | " | " | " |
| 4-$SCH_3$ | " | " | " |
| 4-$C(CH_3)_3$ | " | " | " |
| 4-Cl | —O—$CH_2$— | —$CH(CH_3)_2$ | " |
| 4-F | " | " | " |
| 4-$CH_3$ | " | " | " |
| 4-Cl | " | 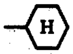 | " |
| 4-F | " | " | " |
| 4-$CH_3$ | " | " | " |
| 4-Cl | " | 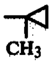 | " |
| 4-F | " | " | " |
| 4-$CH_3$ | " | " | " |
| 4-Cl | —$CH_2$—$CH_2$— | —$CH(CH_3)_2$ | " |
| 4-F | " | " | " |
| 4-$CH_3$ | " | " | " |
| 4-Cl | " | 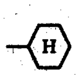 | " |
| 4-F | " | " | " |
| 4-$CH_3$ | " | " | " |

-continued

| $Z_m$ | $Y^2$ | $R^{13}$ | $X^2$ |
|---|---|---|---|
| 4-Cl | " | 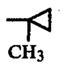 | " |
| 4-F | " | " | " |
| $4-CH_3$ | " | " | " |
| 4-Cl | —CH=CH— | $—CH(CH_3)_2$ | " |
| 4-F | " | " | " |
| $4-CH_3$ | " | " | " |
| 4-Cl | " | 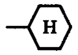 | " |
| 4-F | " | " | " |
| $4-CH_3$ | " | " | " |
| 4-Cl | " | 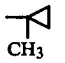 | " |
| 4-F | " | " | " |
| $4-CH_3$ | " | " | " |
| $2,4-Cl_2$ | $—CH_2—CH_2—$ | $—C(CH_3)_3$ | " |
| $4-CH_3$ | " | " | " |
| $4-Cl, 2-CH_3$ | " | " | " |
| $2,4-Cl_2$ | —CH=CH— | " | " |
| $4-CH_3$ | " | " | " |
| $4-Cl, 2-CH_3$ | " | " | " |
| 4-F | $—O—CH_2—$ | " | " |
| $2-CH_3$ | $—CH_2—CH_2—$ | " | N |
| 4-F | —CH=CH— | " | N |

Further particularly preferred azoles of the formula (V) are mentioned in the preparative examples hereinbelow.

The azoles of the formula (V) are hitherto unknown. However, they can be prepared by reacting an oxirane of the general formula

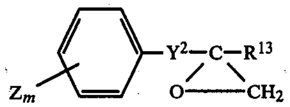

(XII)

in which $R^{13}$, $Y^2$, Z and m have the meanings given above, with an azole of the general formula

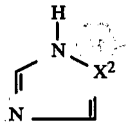

(XIII)

in which $X^2$ has the meaning given above, at a temperature between 60° C. and 150° C. in the presence of a diluent and, if appropriate, in the presence of an acid-binding agent.

Preferred pyrimidine butanol derivatives of the formula (VI), are those, in which $R^{14}$ represents a hydrogen, fluorine, chlorine or bromine atom, and alkyl radical having 1 to 4 carbon atoms or a benzyloxy radical which is optionally substituted by chlorine, and $R^{15}$ represents a hydrogen, fluorine, chlorine or bromine atom.

Very particularly preferred compounds of the formula (VI) are those in which, $R^{14}$ represents a hydrogen, fluorine or chlorine atom or a methyl, ethyl, isopropyl, methoxy, ethoxy, isopropoxy, benzyloxy or chlorobenzyloxy radical and $R^{15}$ represents a hydrogen, chlorine or fluorine atom.

Further specific particularly preferred pyrimidine-butanol derivatives of the formula (VI) are given in the preparative examples hereinbelow.

The pyrimidine-butanol derivatives of the formula (VI) are already known (see DE-A (German Published Specification) No. 2,742,173).

The following preferred acids which are suitable for the preparation of acid addition salts of azoles of the formulae (I), (II), (III), (IV) and (V): the hydrohalic acids (such as hydrochloric acid and hydrobromic acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formulae (I) to (V) can be obtained in a simple manner according to customary methods of salt formation, for example by dissolving a compound of the formulae (I) to (V) in a suitable inert solvent and adding the acid, for example hydrochloric acid, and can be isolated in a known manner, for example by filtering off, and if appropriate, can be purified by washing with an inert organic solvent.

Salts of metals of the main groups II to IV and sub-groups I, II and IV to VIII of the periodic system of the elements are preferred salts for the preparation of metal salt complexes of the compounds of the formulae (I) to (V), copper, zinc, manganese, magnesium, tin, iron and nickel being mentioned by way of example.

Anions which are preferably derived from the following acids are suitable anions of the salts: hydrohalic acids (such as hydrochloric acid and hydrobromic acid), phosphoric acid, nitric acid and sulphuric acid.

The metal complexes of compounds of the formulae (I) to (V) can be obtained in a simple manner according to customary processes, for example by dissolving the metal salt in alcohol, for example ethanol, and adding the solution to a compound of the formulae (I) to (V). The metal salt complexes can be isolated in a known manner, for example by filtering off, and, if appropriate, can be purified by recrystallization.

Preferred phosphonic acid derivatives of the formula (VII) are those in which $R^{16}$ and $R^{17}$ represent a hydrogen atom or a sodium cation.

The phosphonic acid derivatives of the formula (VII) are already known (see DE-A (German Published Specification) No. 3,053,967).

Preferred 1-amino-cyclopropane-1-carboxylic acid derivatives of the formula (VIII) are those in which $R^{18}$ represent a hydroxyl radical, an alkoxy radical having 1 to 20 carbon atoms, a benzyloxy or amino radical, an alkylamino radical having 1 to 4 carbon atoms, a dialkylamino radical having 1 to 4 carbon atoms per alkyl radical, or a radical $O^{\ominus}M^{\oplus}$ wherein $M^{61}$ represents a sodium ion or potassium ion, a magnesium ion equivalent or calcium ion equivalent, ammonium, alkylammonium having 1 to 4 carbon atoms, or dialkylammonium, trialkylammonium or tetraalkylammonium having 1 to 4 carbon atoms per alkyl radical in each case, and $R^{19}$ represents an amino radical or a radical of the general formula —NH—CO—R, wherein R represents a hydrogen atom an alkyl radical having 1 to 4 carbon atoms or a phenyl radical, or a radical $—NH_3Cl^{\ominus}$.

Very particularly preferred compounds of the formula (VIII) are those in which $R^{18}$ represents a hydroxyl radical, an alkoxy radical having 1 to 10 carbon atoms, a benzyloxy or amino radical, an alkylamino radical having 1 or 2 carbon atoms, a dialkylamino radical having 1 or 1 carbon atoms per alkyl radical, or a radical $O^{\ominus}M^{\oplus}$ wherein $M^{\oplus}$ represents a sodium ion or potassium ion, a magnesium ion equivalent or calcium ion equivalent, ammonium, alkylammonium having 1 or 2 carbon atoms, or dialkylammonium, trialkylammonium or tetraalkylammonium having 1 or 2 carbon atoms per alkyl radical in each case, and $R^{19}$ represents amino, formylamino, acetylamino, propionylamino or $NH_3Cl^{\ominus}$.

Further particularly preferred 1-amino-cyclopropane-1-carboxylic acid derivatives of the formula (VIII) are mentioned in the preparative examples hereinbelow.

The 1-amino-cyclopropane-1-carboxylic acid derivatives of the formula (VIII) are already known (see U.S. Pat. No. 4,236,983 issued Dec. 2, 1980.

If the active compounds are present in the active compound combinations according to the invention in certain proportions, the synergistic effect is particularly clearly exhibited. However, the proportions by weight of the active compounds in the active compound combinations can vary within relatively wide ranges. In general, 0.05 to 5 parts by weight, preferably 0.1 to 4 parts by weight, of one of the active compounds listed under (2) are present for 1 part by weight of an active compound listed under (1).

The active compound combinations according to the invention exhibits a powerful plant-growth inhibiting activity, particularly in the case of monocotyledonous plants, such as, for example, cereals and grass.

Inhibiting the growth in length of cereals is important because lodging of the stems of the cereal is thereby largely avoided, even under unfavorable weather conditions. By using the active compound combinations according to the invention, it is also possible to apply a fertilizer containing greater quantities of nitrogeneous fertilizers, without danger of the cereal lodging. Thus, by using the active compound combinations according to the invention in conjunction with the application of a larger quantity of fertilizer, greater yields can be achieved.

The synergistic effect of the active compound combinations according to the invention, which effect has been described, can also be advantageously utilized for inhibiting the growth of grass. It is thus possible, for example, to reduce the frequency of cutting the grass in ornamental gardens, parks and athletic fields or at borders.

Cereals are to be understood in the present case as meaning all customary cereal types. These preferably include oats, rye, barley, wheat and rice.

The active compound combinations can be converted to the customary formulations, such as solutions, emulsions, suspensions, powders and granules.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicylclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic materials such as sawdust, coconut shells, corn cobs and tabacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example ion oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of total active ingredients, preferably from 0.5 to 90 percent by weight.

The active compound combinations according to the invention can be present in the formulations as a mixture with other known active compounds, such as fungicides, insecticides, acaricides and herbicides, and also as mixtures with fertilizers.

The active compound combinations can be used as such, in the form of their formulations or as the use forms prepared therefrom, such as ready-to-use solutions, emulsifiable concentrates, emulsions, suspensions, wettable powders, soluble powders and granules.

They are used in the customary manner, for example by watering, spraying, atomizing and scattering.

The active compound concentrations can be varied within a substantial range. In general, 0.01 to 50 kg, preferably, 0.05 to 10 kg, of the active compound are employed per hectare of soil surface.

The present invention also provides a method of regulating the growth of plants which comprises applying to the plants, or to a habitat thereof, a composition of the present invention.

The present invention further provides plants, the growth of which has been regulated by their being grown in areas in which immediately prior to and/or during the time of the growing a composition of the present invention was applied.

It will be seen that the usual methods of providing a harvested crop may be improved by the present invention.

The good plant-inhibiting action of the active compound combinations according to the invention can be seen from the examples which follow. While the individual active compounds have weaknesses in growth-inhibiting action, the combinations show an action which goes beyond a simple additive action.

A synergistic effect exists with growth inhibitors whenever the growth-inhibiting action of the active compound combinations is greater than the sum of the actions of the individually applied active compounds.

The action to be expected for a given combination of two growth inhibitors can (see Colby, S. R., "Calculating synergistic and antagonistic responses of herbicide combinations", Weeds 15, pages 20-22, 1967) be calculated as follows:

if X = % growth inhibition by active compound A used in an amount of p kg/ha, and Y = % growth inhibition by active compound B used in an amount of q kg/ha, and E = the expected growth inhibition by the active compounds A and B used in amounts of p and q kg/ha, then $$E=X+Y-(X \cdot Y)/100.$$

If the actual growth inhibition is greater than calculated, the action of the combination is superadditive, that is to say a syneergistic effect exists.

The tables in Examples A and B show clearly that the found growth-inhibiting action of the active compound combinations according to the invention is greater than the calculated action, that is to say a synergistic effect exists.

The active compounds indicated below are employed in the examples which follow:

(I-1) = 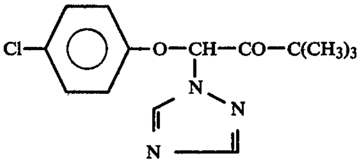

(I-2) = 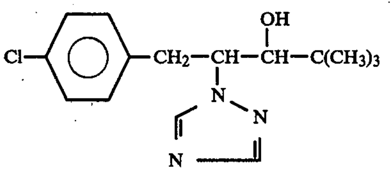

(I-3) = 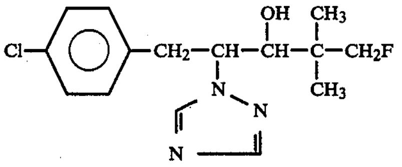

(II-2) = 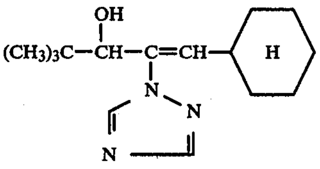

(III-1) = 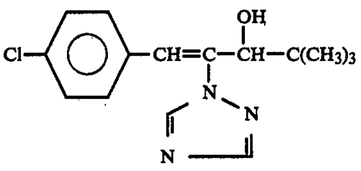

(III-4) = 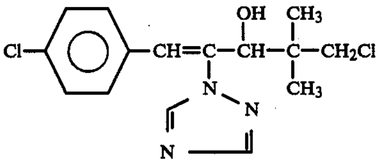

(V-1) = 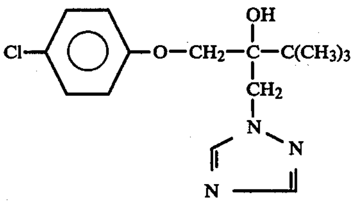

(VI-4) = 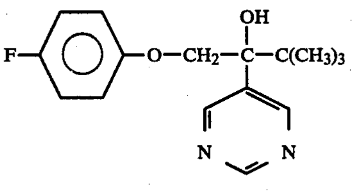

-continued (VII-1) = 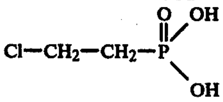

(VIII-17) = 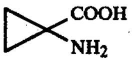

EXAMPLE A

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of the active compounds was mixed with the stated amounts of solvent and emulsifier and the mixture was made up to the desired concentration with water.

Barley plants were grown in a greenhouse to the 2-leaf stage. In this stage, the plants were sprayed with the equivalent of 500 l/ha of the preparations of active compound. After 11 days, the additional growth was measured on all plants and the inhibition of growth in percent of the additional growth of the control plants was calculated. 100% inhibition of growth meant that growth had stopped and 0% denoted a growth corresponding to that of the control plants.

Active compounds, quantities used and test results are indicated in the table which follows.

TABLE A

| Inhibition of growth of barley | | | |
|---|---|---|---|
| Active compounds or combinations | Quantity of active compound used kg/ha | Inhibition of growth in % found* | Inhibition of growth in % calc.* |
| (VIII-17) | 1 | 13 | — |
| (VII-1) | 1 | 12 | — |
| (I-1) | 4 | 13 | — |
| (I-1) | 4 | | |
| | + | 29 | 23.4 |
| (VII-1) | 1 | | |
| (V-1) | 2 | 19 | — |
| (V-1) | 2 | | |
| | + | 50 | 28.7 |
| (VII-1) | 1 | | |
| (I-2) | 2 | 17 | — |
| (I-2) | 2 | | |
| | + | 35 | 27.0 |
| (VII-1) | 1 | | |
| (III-4) | 2 | 8 | — |
| (III-4) | 2 | | |
| | + | 31 | 20.0 |
| (VIII-17) | 1 | | |
| (II-2) | 2 | 17 | — |
| (II-2) | 2 | | |
| | + | 35 | 27.8 |
| (VIII-17) | 1 | | |
| (II-2) | 2 | | |
| | + | 37 | 27.0 |
| (VII-1) | 1 | | |

*found = inhibition of growth found
*calc. = inhibition of growth calculated using the formula given hereinabove

EXAMPLE B

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of the active compounds was mixed with the stated amounts of solvent and emulsifier and the mixture was made up to the desired concentration with water.

Barley plants were grown in a greenhouse to the 2-leaf stage. In this stage, the plants were sprayed with the equivalent of 500 l/ha of the preparations of active compound. After 24 days, the additional growth was measured on all plants and the inhibition of growth in percent of the additional growth of the control plants was calculated. 100% inhibition of growth meant that growth had stopped and 0% denoted a growth corresponding to that of the control plants.

Active compounds, quantities used and test reslts are indicated in the table which follows.

TABLE B

| Inhibition of growth of barley | | | |
|---|---|---|---|
| Active compounds or combinations | Quantity of active compound used kg/ha | Inhibition of growth in % found* | Inhibition of growth in % calc.* |
| (VIII-17) | 1 | 3 | — |
| (VII-1) | 1 | 2 | — |
| (VI-4) | 2 | 25 | — |
| (VI-4) | 2 | | |
| | + | 31 | 27.3 |
| (VIII-17) | 1 | | |
| (V-1) | 2 | 9 | — |
| (V-1) | 2 | | |
| | + | 22 | 10.8 |
| (VII-1) | 1 | | |
| (I-2) | 2 | 5 | — |
| (I-2) | 2 | | |
| | + | 17 | 6.9 |
| (VII-1) | 1 | | |
| (I-3) | 2 | 19 | — |
| (I-3) | 2 | | |
| | + | 25 | 20.6 |
| (VII-1) | 1 | | |
| (III-1) | 2 | 22 | — |
| (III-1) | 2 | | |
| | + | 33 | 24.3 |
| (VIII-17) | 1 | | |
| (II-2) | 2 | 5 | — |
| (II-2) | 2 | | |
| | + | 33 | 7.9 |
| (VIII-17) | 1 | | |
| (II-2) | 2 | | |
| | + | 26 | 6.9 |
| (VII-1) | 1 | | |

*found = inhibition of growth found
*calc. = inhibition of growth calculated using the formula given hereinabove

EXAMPLE C

Inhibition of growth of barley

Aqueous solutions containing 1% by weight of active compound were prepared by mixing the required amount of the formulations, which are described in the formulation examples I to III, with water. Said aqueous solutions were mixed in the desired amounts and diluted with water until the desired concentration was reached.

Barley plants (variety "Gerda") were grown in Neubauer pots (8 plants per pot) in the field. In the 2-node-stage, the plants were sprayed with the equivalent of 500 l/ha of the preparations of the active compounds. After 2 months, the additional growth was measured on all plants and the inhibition of growth in percent of the additional growth of the control plants was calculated. 100% inhibition of growth meant that growth had stopped and 0% denoted a growth corresponding to that of the control plants.

Active compounds, quantities used and test results are indicated in the table which follows.

TABLE C

| Inhibition of growth of barley | | | |
|---|---|---|---|
| Active compounds or combinations | quantity of active compounds used kg/ha | Inhibition of growth in % found* | calc.* |
| (II-2) | 0.25 | 5 | — |
| | 0.5 | 9 | — |
| (VIII-3) | 0.5 | 8 | — |
| (II-2) + (VIII-3) | 0.25 + 0.5 | 21 | 12.6 |
| | 0.5 + 0.5 | 24 | 16.28 |
| (II-2) | 0.125 | 0 | — |
| (VIII-22) | 0.5 | 12 | — |
| (II-2) + (VIII-22) | 0.125 + 0.5 | 19 | 12 |

*found = inhibition of growth found
*calc. = inhibition of growth calculated using the formula given hereinabove

FORMULATION EXAMPLES

EXAMPLE I

For the formulation of a wettable powder
70% by weight of the active compound according to Example (II-2),
2% by weight of a surface active agent,
3% by weight of a dispersing agent on basis of ligninsulphonate,
5% by weight of a product obtained by condensation of cyclohexanone, formaldehyde and sodiumbisulphite,
5% by weight of a highly dispersed silicic acid and
15% by weight of kaolin
were thoroughly mixed in Lödige-mixer and then were finely ground in a Mikronizer 8". EXAMPLE II For the preparation of an emulsifiable concentrate
19.6% by weight of the active compound according to Example (VIII-3),
5.0% by weight of alkylarylpolyglycolether and
75.4% by weight of dimethylformamide
were thoroughly mixed.

EXAMPLE III

For the preparation of an emulsifiable concentrate
30.6% by weight of the active compound according to Example (VIII-22),
10.0% by weight of a surface active agent,
5.0% by weight of alkylarylpolyglycolether and
54.4% by weight of cyclohexanone
were thoroughly mixed.

PREPARATIVE EXAMPLES

Example (I-1)

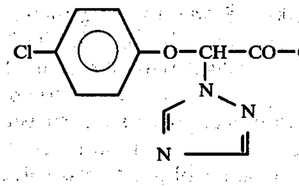

The compound was prepared according to the instructions given in DE-A (German Published Specification) No. 2,407,143.

Example (I-2)

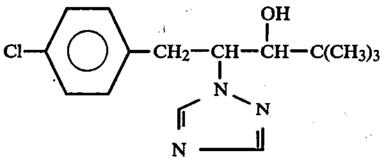

The compound was prepared according to the instructions given in DE-A (German Published Specification) No. 2,737,489.

Example (I-3)

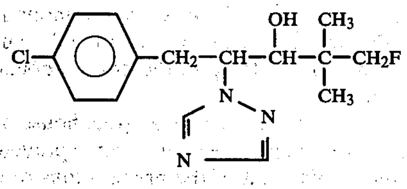

The compound was prepared according to the instructions given in U.S. Application Ser. No. 213,705 filed Dec. 5, 1980, now pending.

The azoles listed in Table 1 which follows were prepared in a corresponding manner.

TABLE 1

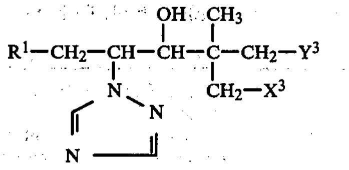

| Example No. | $R^1$ | $X^3$ | $Y^3$ | Melting point (°C.) |
|---|---|---|---|---|
| I-4 | 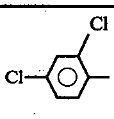 | H | F | 116–121 |
| I-5 | 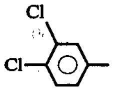 | H | F | 158–174 |
| I-6 | 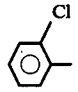 | H | F | 108–112 |
| I-7 | 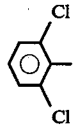 | H | F | 116–122 |
| I-8 | 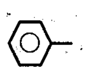 | H | F | 78–88 |
| I-9 | 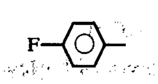 | H | F | 76–84 |
| I-10 | 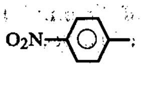 | H | F | 143–154 (decomposition) |

TABLE 1-continued

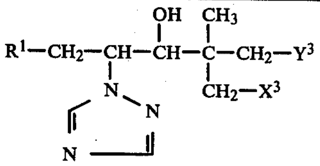

| Example No. | $R^1$ | $X^3$ | $Y^3$ | Melting point (°C.) |
|---|---|---|---|---|
| I-11 | 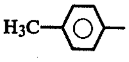 | H | F | 62–72 |
| I-12 | 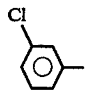 | H | F | 108–128 (decomposition) |
| I-13 | 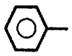 | F | F | 92–111 |
| I-14 | 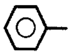 | H | Cl | 82–88 |
| I-15 | 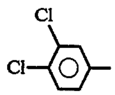 | F | F | 156–168 (decomposition) |
| I-16 | 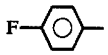 | H | Cl | 98–104 |
| I-17 | 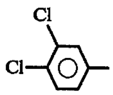 | F | F | 108–126 (decomposition) |
| I-18 | 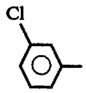 | H | Cl | 108–112 |
| I-19 | 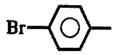 | H | F | 141–144 |
| I-20 | 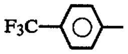 | H | F | 73–76 |
| I-21 | 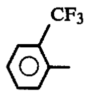 | H | F | 86–92 |

TABLE 1-continued

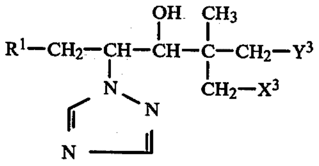

| Example No. | $R^1$ | $X^3$ | $Y^3$ | Melting point (°C.) |
|---|---|---|---|---|
| I-22 | 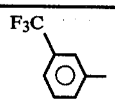 | H | F | 63–68 |
| I-23 | 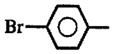 | H | Cl | 108–121 |
| I-24 | 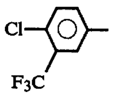 | H | F | 72–112 |
| I-25 | 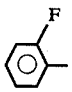 | H | F | 88–98 |
| I-26 | 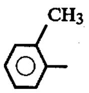 | H | F | 112–123 |
| I-27 | 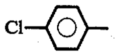 | H | Cl | semi-crystalline |
| I-28 | 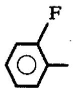 | Cl | Cl | semi-crystalline |
| I-29 | 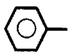 | Cl | Cl | 136–137 |
| I-30 | 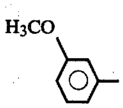 | H | F | 90–108 |
| I-31 | 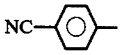 | H | H | 143–146 |

The azoles listed in Table 2 which follows were also prepared according to the method described in Example (I-3).

TABLE 2

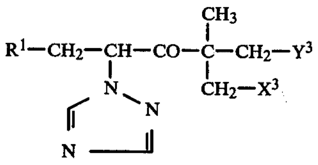

(Ia)

| Example No. | $R^1$ | $X^3$ | $Y^3$ | Melting point (°C.) |
|---|---|---|---|---|
| I-32 | 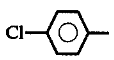 | H | F | 78–79 |

TABLE 2-continued
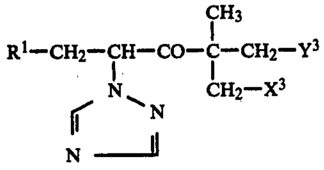
(Ia)
| Example No. | $R^1$ | $X^3$ | $Y^3$ | Melting point (°C.) |
|---|---|---|---|---|
| I-33 | 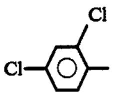 | H | F | 112–120 |
| I-34 | 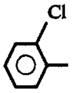 | H | F | 62–72 |
| I-35 | 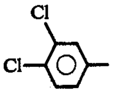 | H | F | 58–70 |
| I-36 | 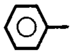 | H | F | 150 (decomposition) (xHCl) |
| I-37 | 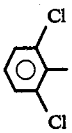 | H | F | 80–92 |
| I-38 | 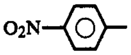 | H | F | 138–140 |
| I-39 | 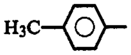 | H | F | 94 |
| I-40 | 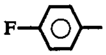 | H | F | 182 (decomposition) (xHCl) |
| I-41 | 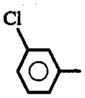 | H | F | 99 |
| I-42 | 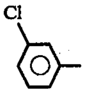 | H | Cl | 102 |
| I-43 | 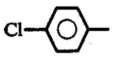 | F | F | 108 |
| I-44 | 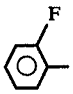 | Cl | Cl | Oil |
| I-45 | 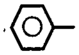 | F | F | Oil |
| I-46 | 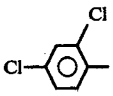 | F | F | 63–78 |

TABLE 2-continued
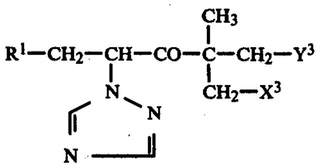
(Ia)
| Example No. | $R^1$ | $X^3$ | $Y^3$ | Melting point (°C.) |
| --- | --- | --- | --- | --- |
| I-47 | 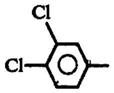 | F | F | 96–112 (decomposition) (xHCl) |
| I-48 | 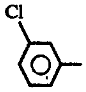 | H | Cl | 116–127 (decomposition) (xHCl) |
| I-49 | 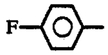 | H | Cl | 58–78 |
| I-50 | 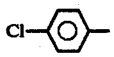 | H | Cl | 58–74 |
| I-51 | 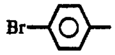 | H | F | 78 |
| I-52 | 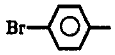 | H | Cl | 56 |
| I-53 | 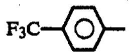 | H | F | 82 |
| I-54 | 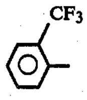 | H | F | 86 |
| I-55 | 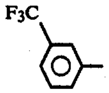 | H | F | 88 |
| I-56 | 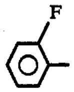 | H | F | 46–48 |
| I-57 | 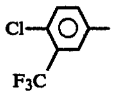 | H | F | 53–63 |
| I-58 | 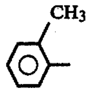 | H | F | 62–64 |
| I-59 | 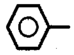 | Cl | Cl | Oil |
| I-60 | 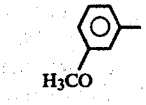 | H | F | 78–81 |

TABLE 2-continued

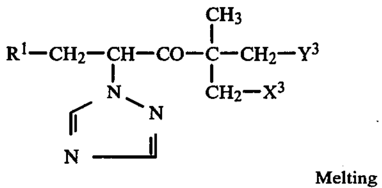
(Ia)

| Example No. | $R^1$ | $X^3$ | $Y^3$ | Melting point (°C.) |
|---|---|---|---|---|
| I-61 | 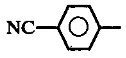 | H | F | 138-141 |

Example (II-1)

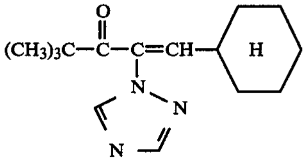

83.5 g (0.5 mol) of pinacolyl-1,2,4-triazole, 60 g (0.54 mol) of cyclohexanaldehyde, 4.2 g (0.05 mol) of piperidine and 6 g (0.1 mol) of glacial acetic acid in 300 ml of toluene were heated under reflux in a water separator until water no longer passed over. After the reaction solution had cooled, it was washed with saturated sodium chloride solution, and the organic phase was dried over sodium sulphate, filtered and concentrated. The residue was taken up in 500 ml of acetone, and a filtered solution of 90 g (0.25 mol) of naphthalene-1,5-disulphonic acid in 500 ml of acetone was added, while stirring.

The precipitate which first separated out was filtered off under suction, the filtrate was further concentrated and the colorless crystalline residue obtained was taken up in 500 ml of methylene chloride. Semiconcentrated sodium carbonate solution was thereafter added to the mixture until an alkaline reaction was obtained. The organic phase was separated off, dried, filtered and concentrated. The oleaginous residue was taken up in petroleum ether and was left to crystallize. 64 g (49% of theory) of 1-cyclohexyl-4,4-dimethyl-2-(1,2,4-triazol-1-yl)-pent-1-en-3-one of melting point 98° C. were obtained.

Example (II-2)

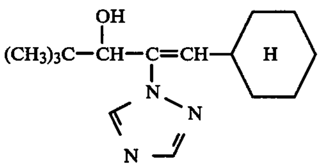

26 g (0.1 mol) of 1-cyclohexyl-4,4-dimethyl-2-(1,2,4-triazol-1-yl)-pent-1-en-3-one (prepared as described in Example II-1) were taken up in 200 methanol, and 4.5 g of sodium borohydride were added in portions to the solution, while stirring and cooling. After the reaction had ended, the reaction mixture was adjusted to pH 6 and was concentrated. The residue was taken up in 200 ml of methylene chloride, and the solution was washed with saturated sodium bicarbonate solution, dried over sodium sulphate, filtered and concentrated. The residue was recrystallized from petroleum ether. 14.5 g (55% of theory) of 1-cyclohexyl-4,4-dimethyl-2-(1,2,4-triazol-1-yl)-pent-1-en-3-ol of melting point 131° C. were obtained.

Example (II-3)

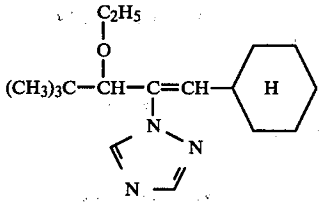

A solution of 26.3 g (0.1 mol) of 1-cyclohexyl-4,4-dimethyl-2-(1,2,4-triazol-1-yl)-pent-1-en-3-ol (prepared as described in Example II-2) in 50 ml of dioxane was added dropwise to a suspension of 3 g of 80% strength sodium hydride in 100 ml of dioxane. After the addition had ended, the mixture was warmed to 50° C. for 1 hour. After the mixture had cooled, 10.9 g (0.1 mol) of ethyl bromide were added dropwise to it, and the reaction mixture was heated under reflux overnight. After the mixture had cooled, 10 ml of methanol were added to it and it was concentrated in a rotary evaporator. The residue was taken up in methylene chloride and was washed with water. After the organic phase had been dried over sodium sulphate, it was filtered and the filtrate was concentrated. The residue was distilled. 11.0 g (37.8% of theory) of 1-cyclohexyl-3-ethoxy-4,4-dimethyl-2-(1,2,4-triazol-1-yl)-pent-1-ene of boiling point 110° C./0.07 mm Hg were obtained.

Example (II-4)

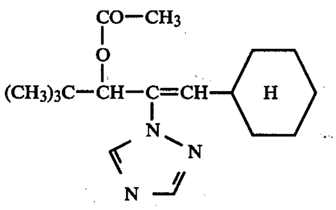

A solution of 13.15 g (0.05 mol) of 1-cyclohexyl-4,4-dimethyl-2-(1,2,4-triazol-1-yl)-pent-1-en-3-ol (prepared as described in Example II-2) in 50 ml of dioxane was added dropwise to a suspension of 1.5 g of 80% strength sodium hydride in 50 ml of dioxane. After the evolution of hydrogen had ceased, 3.9 g (0.05 mol) of acetyl chloride were added dropwise to the mixture. The mixture was heated under reflux for 4 hours. After the mixture had cooled, the solvent was distilled off in vacuo, and the residue was taken up in methylene chloride and the solution was extracted with water. The organic phase was dried over sodium sulphate and filtered, and the solution was concentrated. The residue was purified over a column (silica gel; methanol: chloroform=1:3). 5.6 g (35.4% of theory) of 3-acetoxy-1-cyclohexyl-4,4-dimethyl-2-(1,2,4-triazol-1-yl)-pent-1-ene were obtained as a slightly yellow oil. 2 ml of pyridine were added to a solution of 13.15 g (0.05 mol) of 1-cyclohexyl-4,4-dimethyl-2-(1,2,4-triazol-1-yl)-pent-1-en-3-ol (prepared as described in Example II-2) in 100 ml of acetic anhydride. The mixture was stirred for four hours at 70° C. The reaction mixture was thereafter poured onto water and was neutralized with sodium bicarbonate. The aqueous phase was extracted several times with ether. The combined ether phases were dried over sodium sulphate and concentrated. 11.2 g (70.8% of theory) of 3-acetoxy-1-cyclohexyl-4,4-dimethyl-2-(1,2,4-triazol-1-yl)-pent-1-ene were obtained as a slightly yellow oil.

Example (II-5)

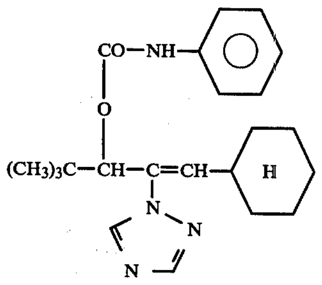

6.5 g (0.055 mol) of phenyl isocyanate and three drops of tributyltin laurate as a catalyst were added to a solution of 13.15 g (0.05 mol) of 1-cyclohexyl-4,4-dimethyl-2-(1,2,4-triazol-1-yl)-pent-1-en-3-ol (prepared as described in Example II-2) in 100 ml of ether. The mixture was stirred for 5 days at room temperature. After the solvent had been distilled off in vacuo, the residue was recrystallized from ethyl acetate/ligroin. 4.8 g (25.1% of theory) of 1-cyclohexyl-4,4-dimethyl-3-phenylcarbamoyloxy-2-(1,2,4-triazol-1-yl)-pent-1-ene of melting point 156° C. were obtained.

The compounds below were obtained in an analogous manner:

TABLE 3

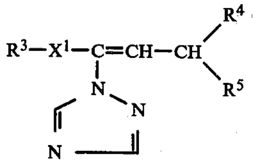

(IId)

| Example No. | $R^3$ | $X^1$ | $R^4$ | $R^5$ | Melting point (°C.) |
|---|---|---|---|---|---|
| II-6 | $(CH_3)_3C$ | —CO— | 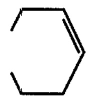 | | 193 (× ½ NDA) |
| II-7 | $(CH_3)_3C$ | —CO— | 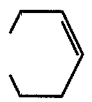 | | 40–48 |
| II-8 | $(CH_3)_3C$ | —CO— | 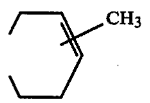 | | 49 |
| II-9 | $(CH_3)_3C$ | —CO— | 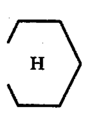 | | 201 (× ½ NDA) |
| II-10 | $(CH_3)_3$ | —CO— | n-$C_4H_9$ | $C_2H_5$ | Oil |
| II-11 | $(CH_3)_3C$ | —CH(OH)— | 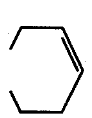 | | 151 (Z Form) |

TABLE 3-continued
| | | | | |
|---|---|---|---|---|
| II-12 | $(CH_3)_3C$ | $-CH(OH)-$ | 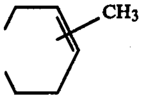 | Oil |
| II-13 | $(CH_3)_3C$ | $-CH(OC_3H_7-n)-$ | 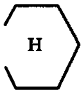 | Oil |
| II-14 | $(CH_3)_3C$ | $-CH(O-CO-$ 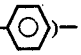 $)-$ | 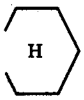 | Oil |
| II-15 | $(CH_3)_3C$ | $-CH(O-CO-CHCl_2)-$ | 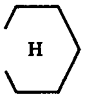 | Oil |
| II-16 | $(CH_3)_3C$ | 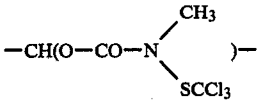 | 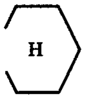 | Oil |
| II-17 | 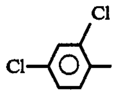 | $-CH(OH)-$ | 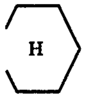 | Oil |
| II-18 | 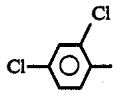 | $-CH(OH)-$ | $C_2H_5$ $C_2H_5$ | Oil |
| II-19 | 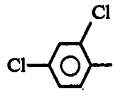 | $-CH(OH)-$ | 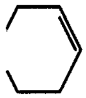 | Oil |
| II-20 | 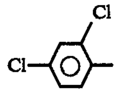 | $-CH(O-COCH_3)-$ | 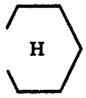 | Oil |
| II-21 | $(CH_3)_3C$ | $-CCH_3(OH)-$ | 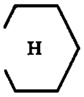 | 101 |
| II-22 | $(CH_3)_3C$ | $-CH(OH)-$ | 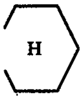 | 154 (.HCl) (Z Form) |
| II-23 | 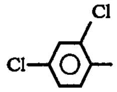 | $-CH(OH)-$ | $C_3H_7$ $CH_3$ | Oil |
| II-24 | $(CH_3)_3C$ | $-CH(OH)-$ | 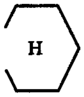 | 110 (.$CuCl_2$) (Z Form) |
| II-25 | 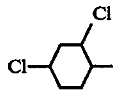 | $-CH(O-CO-NHCH_3)-$ | 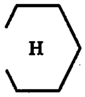 | 62 |

TABLE 3-continued
| | | | | | |
|---|---|---|---|---|---|
| II-26 | 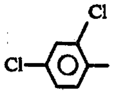 | —CH(OH)— | $C_2H_7$ | $CH_3$ | Oil |
| II-27 | 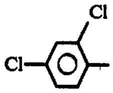 | 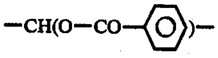 | $C_3H_7$ | $CH_3$ | Oil |
| II-28 | 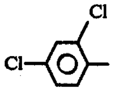 | —CH(O—CO—$CH_3$)— | $C_3H_7$ | $CH_3$ | Oil |
| II-29 | $(CH_3)_3C$ | 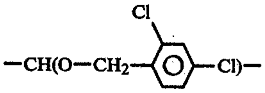 | 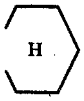 | | Oil (Z Form) |
| II-30 | $ClCH_2$—$C(CH_3)_2$— | —CO— | 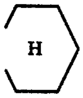 | | 51 |
| II-31 | $ClCH_2$—$C(CH_3)_2$— | —CO— | 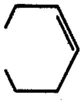 | | Oil |
| II-32 | $ClCH_2$—$C(CH_3)_2$— | —CH(OH)— | 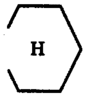 | | Oil |
| II-33 | 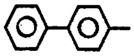 | —CH(OH)— | 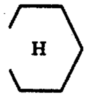 | | 156 |
| II-34 | $(CH_3)_3C$ | —CH(OH)— | 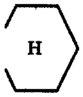 | | 153 (.$HNO_3$) (Z Form) |
| II-35 | 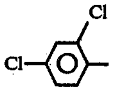 | —CH(OH)— | 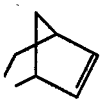 | | Oil |
| II-36 | 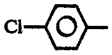 | —CH(OH)— | 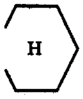 | | Oil |
| II-37 | 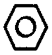 | —CH(OH)— | 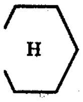 | | Oil |
| II-38 | 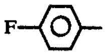 | —CH(OH)— | $C_2H_5$ | $CH_3$ | Oil |
| II-39 | 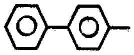 | —CH(OH)— | $C_2H_5$ | $CH_3$ | Oil |
| II-40 | 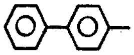 | —CH(OH)— | $C_4H_9$ | $C_2H_5$ | Oil |

TABLE 3-continued

| | | | | | |
|---|---|---|---|---|---|
| II-41 | $ClCH_2-C(CH_3)_2-$ | $-CH(OH)-$ | 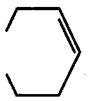 | | Oil |
| II-42 | $(CH_3)_3C$ | $-CH(OCH_3)-$ | 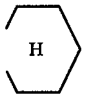 | | 63 (Z Form) |
| II-43 | 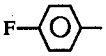 | $-CH(OH)-$ | $C_4H_9$ | $C_2H_5$ | Oil |
| II-44 | $FCH_2-C(CH_3)_2-$ | $-CO-$ | $C_4H_9$ | $C_2H_5$ | Oil |
| II-45 | $(CH_3)_3C$ | $-CH(OCH_3)-$ | 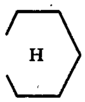 | | 104 (E Form) |
| II-46 | $(CH_3)_3C$ | $-CH(OH)-$ | 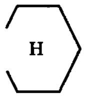 | | 137 (.$HNO_3$) (E Form) |
| II-47 | 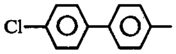 | $-CH(OH)-$ | $CH_3$ | $CH_3$ | 187 |
| II-48 | $ClCH_2-C(CH_3)_2-$ | $-CH(OH)-$ | $CH_3$ | $CH_3$ | Oil |
| II-49 | $(CH_3)_3C$ | $-CH(OH)-$ | 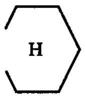 | | 242 (.½ NDA) (E Form) |
| II-50 | $(CH_3)_3C$ | $-CH(OH)-$ | 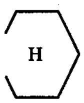 | | 168 (.$CuCl_2$) (E Form) |
| II-51 | $(CH_3)_3C$ | $-CO-$ | 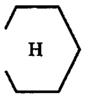 | | 137-140 (.$CuCl_2$) (E Form) |
| II-52 | 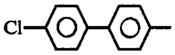 | $-CH(OH)-$ | 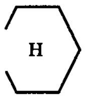 | | 157 |
| II-53 | 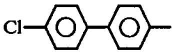 | $-CH(OH)-$ | $C_4H_9$ | $C_2H_5$ | 118 |
| II-54 | $FCH_2-C(CH_3)_2-$ | $-CO-$ | 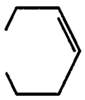 | | Oil |
| II-55 | $FCH_2-C(CH_3)_2-$ | $-CO-$ | 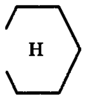 | | Oil |
| II-56 | $FCH_2-C(CH_3)_2-$ | $-CH(OH)-$ | 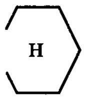 | | Oil |

TABLE 3-continued
| | | | | |
|---|---|---|---|---|
| II-57 | $FCH_2-C(CH_3)_2-$ | $-CH(OH)-$ | 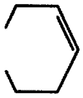 | Oil |
| II-58 | $FCH_2-C(CH_3)_2-$ | $-CO-$ | 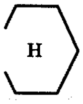 | Oil (Z Form) |
| II-59 | $FCH_2-C(CH_3)_2-$ | $-CO-$ | 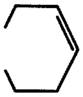 | Oil (Z Form) |
| II-60 | $ClCH_2-C(CH_3)_2-$ | $-CO-$ | 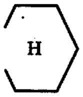 | 103 (E Form) |
| II-61 | 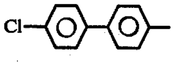 | $-CH(OH)-$ | | 144 |
| II-62 | 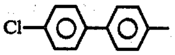 | $-CH(OH)-$ | $C_2H_5$ $C_2H_5$ | 148 |
| II-63 | $FCH_2-C(CH_3)_2-$ | $-CH(OH)-$ | 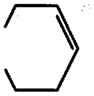 | $n_D^{20}$: 1.5049 (Z Form) |
| II-64 | $FCH_2-C(CH_3)_2-$ | $-CH(OH)-$ | 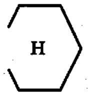 | $n_D^{20}$: 1.4910 (Z Form) |
| II-65 | $ClCH_2-C(CH_3)_2-$ | $-CH(OH)-$ | 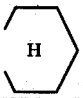 | $n_D^{20}$: 1.5050 (E Form) |
E form and Z form = the two possible geometric isomeric forms
NDA = 1,5-Naphthalenedisulphonic acid Example III-1

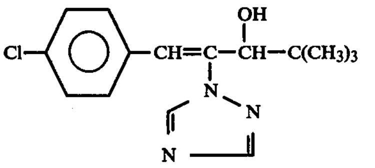

B form

The compound was prepared according to the method giving in U.S. Application Ser. No. 144,110 filed Apr. 28, 1980, now pending.

Example III-2

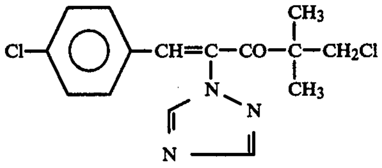

E/Z isomer mixture

Example III-3

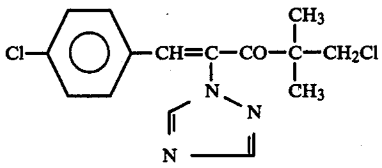

E isomer 210.5 g (1 mol) of 1-chloro-2,2-dimethyl-4-(1,2,4-triazol-1-yl)-butan-3-one, 140.5 g (1 mol) of 4-chlorobenzaldehyde and 9.9 ml of piperidine and 30 g of glacial acetic acid were heated under reflux in 300 ml of toluene for 8 hours, the resulting water of reaction being removed azeotropically. The reaction mixture was thereafter washed with water and with dilute sodium bicarbonate solution, dried over sodium sulphate and concentrated in vacuo. 305.9 g (94.4% of theory) of crude 1-chloro-5-(4-chlorophenyl)-2,2-dimethyl-4-(1,2,4-triazol-1-yl)-4-penten-3one of boiling point 155° C./0.1 mm Hg were obtained as an E,Z isomer mixture. The E isomer could be isolated in crystalline form by stirring the isomer mixture with isopropanol or ethanol. It had a melting point of 112° C.

Example (III-4)

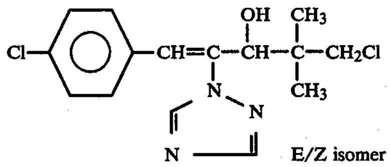

E/Z isomer mixture 162 g (0.5 mol) of 1-chloro-5-(4-chlorophenyl)-2,2-dimethyl-4-(1,2,4-triazol-1-yl)-4-penten-3-one (prepared as described in Example III-2) were dissolved in 500 ml of isopropanol, and 9.5 g (0.25 mol) of sodium borohydride were added in portions to the solution, while stirring. The reaction mixture was stirred for 10 hours at room temperature, and was then concentrated in vacuo. The residue was taken up in toluene, and the solution was washed with dilute acetic acid and then with water, and was dried over sodium sulphate and concentrated in vacuo. 156.6 g (96% of theory) of 1-chloro-5-(4-chlorophenyl)-2,2-dimethyl-4-(1,2,4-triazol-1-yl)-4-penten-3-ol of refractive index $n_D^{20}=1.5579$ were obtained as an E/Z isomer mixture.

Example III-5

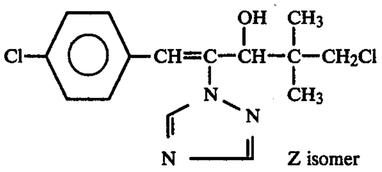

Z isomer 48.6 g (0.15 mol) of 1-chloro-5-(4-chlorphenyl)-2,2-dimethyl-4-(1,2,4-triazol-1-yl)-4-penten-3-one (prepared as described in Example III-2) and 30.6 g (0.15 mol) of aluminum isopropylate were heated under reflux in 200 ml of isopropanol for 7 hours, isopropanol and acetone being continuously distilled off over a 30 cm Vigreux column until acetone could no longer be detected in the distillate. The reaction mixture was thereafter concentrated, and ice/hydrochloric acid was added to the residue. The mixture was extracted with methylene chloride. The combined methylene chloride extracts were dried over sodium sulphate and concentrated in vacuo. The oleaginous residue was separated by column chromatography (silica gel/chloroform). The unreduced E isomer of 1-chloro-5-(4-chlorophenyl)-2,2-dimethyl-4-(1,2,4-triazol-1-yl) penten-3-one (the compound given in Example III-2) and the Z isomer of pure 1-chloro-5-(4-chlorophenyl)-2,2-dimethyl-4-(1,2,4-triazol-1-yl)-penten-3-ol with a melting point of 120° C. were obtained.

Example (III-6)

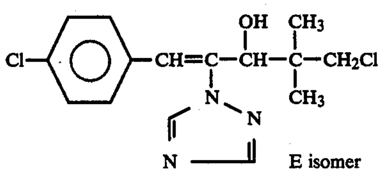

E isomer 2.0 g (6.13 mol) of the E isomer of 1-chloro-5-(4-chlorophenyl)-2,2-dimethyl-4-(1,2,4-triazol-1-yl)-4-penten-3-one (prepared as described in Example III-3) and 0.467 g (4.11 mol) of calcium chloride were dissolved in 30 ml of isopropanol, and a solution of 0.167 g (4.3 mmol) of sodium borohydride was added dropwise to the above solution at −5° C. After 6 hours, the reaction mixture was warmed to 25° C. and was concentrated in vacuo. The residue was poured onto water, and the mixture was extracted with ethyl acetate. The combined ethyl acetate extracts were dried over sodium sulphate and concentrated in vacuo. The oleaginous residue crystallized on stirring it with diisopropyl ether. 1.1 g (55% of theory) of 1-chloro-5-(4-chlorophenyl)-2,2-dimethyl-4-(1,2,4-triazol-1-yl)-4-penten-3-ol of melting point 170° C. were obtained as the E isomer.

The following compounds of the general formula (III) were obtained in a corresponding manner.

TABLE 3
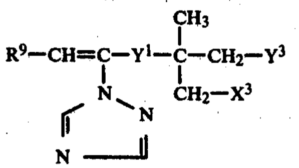
(IIIb)
| Example No. | $R^9$ | $Y^1$ | $X^3$ | $Y^3$ | Melting point (°C.) or refractive index ($n^{20}$) |
|---|---|---|---|---|---|
| III-7 | 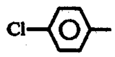 | CO | H | F | 1.5672 |
| III-8 | 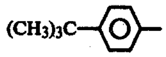 | CO | H | F | 1.5565 |
| III-9 | 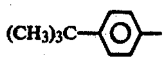 | CO | H | Cl | 1.5655 (Z Isomer) |
| III-10 | 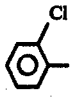 | CO | H | F | 1.5632 (E Isomer) |
| III-11 | 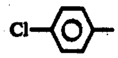 | CH(OH) | H | F | 230 (× NDA) |
| III-12 | 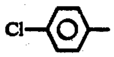 | CH(OH) | H | F | 110 (Z Isomer) |
| III-13 | 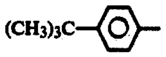 | CH(OH) | H | F | 1.5250 |
| III-14 | 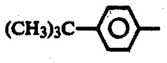 | CH(OH) | H | Cl | 1.5820 (Z Isomer) |
| III-15 | 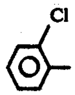 | CH(OH) | H | F | 116 (Z Isomer) |
| III-16 | 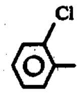 | CH(OH) | H | F | 140 (E Isomer) |
| III-17 | 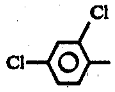 | CH(OH) | H | F | 150 (Z Isomer) |
| III-18 | 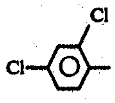 | CH(OH) | H | F | 158 (E Isomer) |
| III-19 | 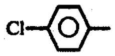 | CO | F | F | 1.5728 |
| III-20 | 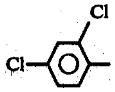 | CO | F | F | 1.5778 |
| III-21 | 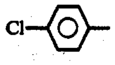 | CO | Cl | Cl | 1.5942 |
| III-22 | 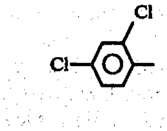 | CO | Cl | Cl | 1.5868 |

TABLE 3-continued

| | | | | | |
|---|---|---|---|---|---|
| III-23 | 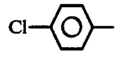 | (CH)OH | F | F | 74 (E Isomer) |
| III-24 | 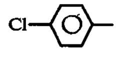 | CH(OH) | F | F | 110 (Z Isomer) |
| III-25 | 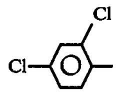 | CH(OH) | F | F | 157 (E Isomer) |
| III-26 | 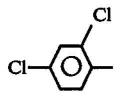 | CH(OH) | F | F | 154 (Z Isomer) |
| III-27 | 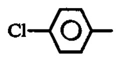 | CH(OH) | Cl | Cl | 150 (Z Isomer) |
| III-28 | 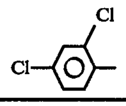 | CH(OH) | Cl | Cl | 148 (Z Isomer) |

NDA = 1,5-Naphthalenedisulphonic acid

Example (V-1)

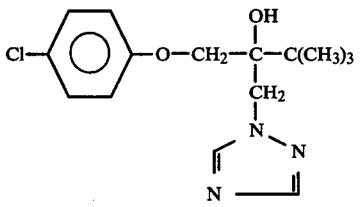

72.15 g (0.3 mol) of 2-(4-chlorophenoxy-methyl)-2-tert.-butyl-oxirane and 24.15 g (0.35 mol) of 1,2,4-triazole were heated under refulx in 120 ml of ethanol for 48 hours. The mixture was then concentrated, and the residue was taken up in 200 ml of ethyl acetate and the solution heated. The solution was thereafter cooled in an ice bath, and the solid material was filtered off under suction and was washed with ethyl acetate. The filtrate was concentrated and the residue was dissolved in ether/hexane, and the solution was treated with gaseous hydrogen chloride. The precipitate was filtered off under suction and washed with ether, and the free base was obtained by the addition of ethyl acetate/1 N sodium hydroxide solution. 60.2 g (65% of theory) of 2-(4-chlorophenoxy-methyl)-3,3-dimethyl-1-(1,2,4-triazol-1-yl)-butan-2-ol of melting point 84°-87° C. were obtained.

Preparation of the starting material

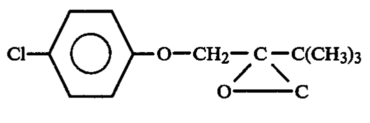

A solution of 162 ml (2.2 mols) of dimethyl sulphide in 400 ml of absolute acetonitrile was added to a solution of 189 ml (2.0 mols) of dimethyl sulphate in 1,200 ml of absolute acetonitrile at room temperature. The reaction mixture was stirred overnight at room temperature. 118.8 g (2.2 mols) of sodium methylate were thereafter added to the mixture. The mixture was stirred for 30 minutes, and a solution of 272 g (1.2 mols) of 1-(4-chlorophenoxy)-3,3-dimethyl-butan-2-one in 600 ml of absolute acetonitrile was added dropwise to it during the course of 30 minutes. The reaction mixture was further stirred overnight and was then concentrated, and the residue was partitioned between water and ethyl acetate. The organic phase was separated off, washed twice with water and once with saturated sodium chloride solution, dried over sodium sulphate and concentrated, and the residue was distilled in vacuo. 242.4 g (84% of theory) of 2-(4-chlorophenoxy-methyl)-2-tert.-butyl-oxirane of boiling point 115°-122° C./0.003 mm Hg and melting point 50°-52° C. were obtained.

Example (V-2)

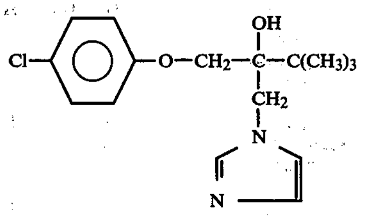

8.02 g (0.1178 mol) of imidazole were added to 2.71 g (0.1178 mol) of sodium in 250 ml of absolute ethanol. A solutin of 14.17 g (0.0589 mol) of 2-(4-chlorophenoxy-methyl)-2-tert.-butyl-oxirane in 100 ml of ethanol was added dropwise to the mixture at room temperature during the course of 30 minutes. The reaction mixture was thereafter heated under reflux for 8 hours and was concentrated, and the residue was taken up in ether. The ether solution was extracted three times with 1 N hydrochloric acid, and the combined hydrochloric acid phases were neutralized with sodium bicarbonate and then extracted with ethyl acetate. After the solution had been concentrated and the residue recrystallized from cyclohexane, 11.6 g (64% of theory) of 2-(4-chloro-phenoxy-methyl)-3,3-dimethyl-1-(imidazol-1-yl)-butan-2-ol of melting point 154°–155° C. were obtained.

Example (V-3)

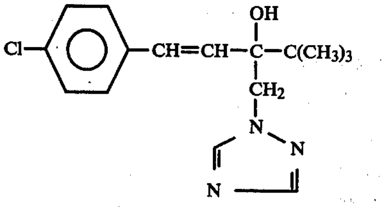

A solution of 17.75 g (0.075 mol) of 2-(4-chlorophenyl-ethenyl)-2-tert.-butyl-oxirane and 6.9 g (0.1 mol) of 1,2,4-triazole in 30 ml of ethanol was heated in a bomb tube at 150° C. for 20 hours. The reaction mixture was thereafter concentrated, and the crystalline residue was stirred with ether. The solid material was then filtered off under suction and was recrystallized from acetonitrile. 17.7 g (77% of theory) of 1-(4-chloro-phenyl)-4,4-dimethyl-3-(1,2,4-triazol-1-yl)-1-penten-3-ol of melting point 139°–141° C. were obtained.

Example (V-4)

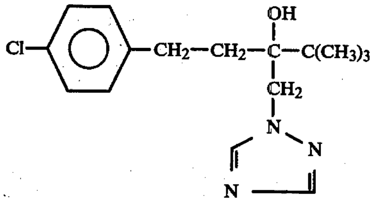

A solution of 17.9 g (0.075 mol) of 2-(4-chlorophenyl-ethyl)-2-tert.-butyl-oxirane and 6.9 g (0.1 mol) of 1,2,4-triazole in 30 ml of ethanol was heated in a bomb tube at 150° C. for 20 hours. The reaction solution was allowed to cool and was concentrated. The residue was dissolved in ether, and the solution was washed three times with water and once with sodium chloride solution, and was dried over sodium sulphate and concentrated. The residue was subjected to chromatography over a silica gel column (eluent: dichloromethane/ethyl acetate 1:1). 12.3 g (53.2% of theory) of 1-(4-chlorophenyl)-4,4-dimethyl-3-(1,2,4-triazol-1-yl-methyl)-pentan-3-ol were obtained as a viscous oil.

The following compounds of the general formula (V) were obtained in an analogous manner:

TABLE 4

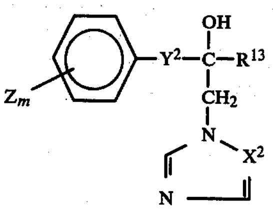

(V)

| Example No. | $Z_m$ | $Y^2$ | $R^{13}$ | $X^2$ | Melting point (°C.) |
|---|---|---|---|---|---|
| V-5 | 4-Cl, 2-$CH_3$ | $-O-CH_2-$ | $-C(CH_3)_3$ | N | 125.5–29 |
| V-6 | 2,4-$Cl_2$ | $-O-CH_2-$ | $-C(CH_3)_3$ | N | 120.5–23.5 |
| V-7 | 4-$CH_3$ | $-O-CH_2-$ | $-C(CH_3)_3$ | N | 98–101.5 |
| V-8 | 2-$CH_3$ | $-O-CH_2-$ | $-C(CH_3)_3$ | N | 89–101 |
| V-9 | 4-F | $-CH_2-CH_2-$ | $-C(CH_3)_3$ | N | 91–95.5 |
| V-10 | 2-$CH_3$ | $-CH=CH-$ | $-C(CH_3)_3$ | N | Oil |
| V-11 | 4-Cl | $-CH_2-CH_2-$ | $-C(CH_3)_3$ | N | 212 (decomposition) (xHCl) |
| V-12 | 2,4-$Cl_2$ | $-O-CH_2-$ | $-C(CH_3)_3$ | CH | 152–54 |
| V-13 | 4-$CH_3$ | $-O-CH_2-$ | $-C(CH_3)_3$ | CH | 129–31 |
| V-14 | 2-$CH_3$ | $-O-CH_2-$ | $-C(CH_3)_3$ | CH | 123–24 |
| V-15 | 4-Cl, 2-$CH_3$ | $-O-CH_2-$ | $-C(CH_3)_3$ | CH | 157–59 |
| V-16 | 4-Cl | $-CH_2-CH_2-$ | $-C(CH_3)_3$ | CH | 157.5–59.5 |
| V-17 | 4-F | $-CH_2-CH_2-$ | $-C(CH_3)_3$ | CH | 124–25 |
| V-18 | 2-$CH_3$ | $-CH_2-CH_2-$ | $-C(CH_3)_3$ | CH | 94–99 |
| V-19 | 4-Cl | $-CH=CH-$ | $-C(CH_3)_3$ | CH | 158.5–62 |
| V-20 | 4-F | $-CH=CH-$ | $-C(CH_3)_3$ | CH | 144–46 |
| V-21 | 2-$CH_3$ | $-CH=CH-$ | $-C(CH_3)_3$ | CH | 127–32 |
| V-22 | 4-Cl | $-O-CH_2-$ | 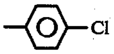 | CH | 216–17 (x ½ NDA*) |
| V-23 | 4-$CH_3$ | $-CH=CH-$ | $-C(CH_3)_3$ | N | 117–19 |
| V-24 | 4-$CH_3$ | $-CH=CH-$ | $-C(CH_3)_3$ | CH | 144–46 |
| V-25 | 2,6-$Cl_2$ | $-CH=CH-$ | $-C(CH_3)_3$ | CH | 110–16 |
| V-26 | 4-$CH_3$ | $-CH_2-CH_2-$ | $-C(CH_3)_3$ | N | Oil |

*NDA = 1,5-Naphthalenedisulphonic acid

Example (VI-1)

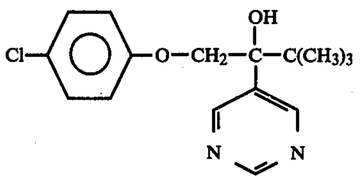

A solution of 22.65 g (0.1 mol) of 1-(4-chlorophenoxy)-3,3-dimethyl-butan-2-one in 110 ml of absolute tetrahydrofuran and 70 ml of absolute ether was cooled to −120° C. under a dry nitrogen atomosphere. A solution of 15.9 g (0.1 mol) of 5-bromopyrimidine in 50 ml of absolute tetrahydrofuran was added dropwise to the above solution. 50 ml of a 15% strength solution of n-butyllithium in n-hexane was then slowly added dropwise to the mixture at −120° C. The mixture was first stirred for 2 hours at a temperature of approximately −110° C., and was thereafter stirred overnight at −78° C. The reaction mixture was warmed to room temperature and 100 ml of 10% strength ammonium chloride solution and 200 ml of ethyl acetate were added to it, and the aqueous phase was separated off. The organic phase was washed successively once with 1 N hydrochloric acid and twice with saturated sodium chloride solution, and was dried over sodium sulphate and concentrated. The residue was suspended in ether, and the solid material was filtered off under suction and recrystallized from acetonitrile. 12.3 g (50% of theory relative to n-butyllithium) of 1-(4-chlorophenoxy)-3,3-dimethyl-2-(pyrimidin-5-yl)-butan-2-olof melting point 172°–174° C. were obtained.

The compounds of the formula

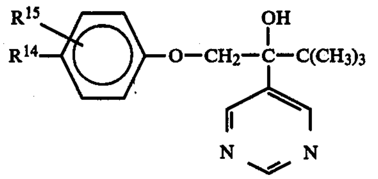

(VI)

which are listed in Table 5 which follows, were obtained analogously:

TABLE 5

| Example No. | $R^{14}$ | $R^{15}$ | Melting point (°C.) |
|---|---|---|---|
| VI-2 | H | H | 127-129 |
| VI-3 | $CH_3O-$ | H | 136-137 |
| VI-4 | F | H | 163.5-164.5 |
| VI-5 | Cl | 2-Cl | 96-99 |
| VI-6 | Cl | 3-Cl | 155-157 |
| VI-7 | $CH_3$ | H | 152-153.5 |
| VI-8 | 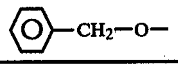 | H | 122-124 |

Example (VIII-1)

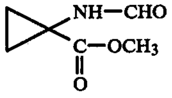

0.3 ml of concentrated hydrochloric acid and a solution of 5 g (0.04 mol) of α-isocyanocyclopropanecarboxylic acid methyl ester in 10 ml of methanol were added successively to 40 ml of water at 20° C. The reaction mixture was stirred for 6 hours and was then extracted with twice 50 ml of methylene chloride. The organic phase was dried over magnesium sulphate and filtered, and the solvent was distilled off in vacuo. 4 g (70% of theory) of α-formylamino-cyclopropane-carboxylic acid methyl ester remained as the residue in the form of a colorless liquid. Refractive index: $n_D^{20}$ =1.4730.

Example (VIII-2)

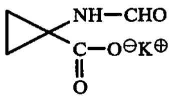

A solution of 3.1 g (0.55 mol) of potassium hydroxide in 50 ml of ethanol was added dropwise to a solution of 7 g (0.05 mol) of α-isocyano-cyclopropanecarboxylic acid ethyl ester in 100 ml of ether at 5° C. The mixture was stirred for 12 hours at 20° C. After the mixture had been filtered under suction and the residue washed with ether, 6.4 g (86% of theory) of the potassium salt of α-isocyano-cyclopropanecarboxylic acid were obtained as a white powder. Melting point: 225° C.

1.18 g (0.066 mol) of water were added to a suspension of 9 g (0.06 mol) of the potassium salt of α-isocyano-cyclopropanecarboxylic acid in 50 ml of ethanol. The mixture was heated to the boil under reflux for 12 hours, and after it had been cooled, 50 ml of ether were added to it at 20° C. After the mixture had been filtered under suction, 7 g (70% of theory) of the potassium salt of α-formylaminocyclopropanecarboxylic acid were obtained in the form of white crystals. Melting point: 186° C.

Example (VIII-3)

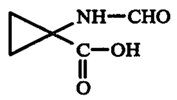

8.36 g (0.05 mol) of the potassium salt of α-formylaminocyclopropanecarboxylic acid were dissolved in 20 ml of water, and 5 g (0.05 mol) of concentrated hydrochloric acid were added to the solution at 0° C. The mixture was left to stand overnight at 5° C. After the mixture had been filtered under suction and the residue dried, 5.2 g (80% of theory) of α-formylaminocyclopropanecarboxylic acid were obtained in the form of colorless crystals. Melting point: 189° C.

Example (VIII-4)

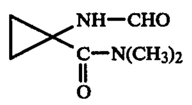

7.46 g (0.05 mol) of the potassium salt of α-isocyanocyclopropanecarboxylic acid were added to a solution of 6.7 g (0.15 mol) of dimethylamine in 50 ml of water at 20° C., while stirring. After the reaction mixture had cooled to 5° C., 5 g (0.05 mol) of concentrated hydrochloric acid were added to it, and it was left to stand for 12 hours at 20° C. in a closed reaction vessel. The volatile components were stripped off in the vacuum from a water jet, at a bath temperature of 60° C. The product was extracted from the residue with methylene chloride; the solution was dried with magnesium sulphate, and, after filtration, the solvent was distilled off in vacuo. 5.5 g (70% of theory) of α-formylamino-cyclopropanecarboxylic acid N,N-dimethylamide remained, in the form of a pale yellow liquid. Refractive index: $n_D^{20}=1.4350$.

Example (VIII-5)

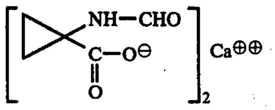

0.74 g (0.01 mol) of clacium hydroxide was added to a mixture of 2.5 g (0.02 mol) of α-formylaminocyclopropanecarboxylic acid and 40 ml of ethanol at 25° C., while stirring, and the mixture was then further stirred for 12 hours at room temperature. The solution was then evaporated in vacuo, and the residue was triturated with ether. After the mixture had been filtered under suction and the residue dried, 2.6 g (97% of theory) of the calcium salt of αformylamino-cyclopropanecarboxylic acid were obtained in the form of a white powder. Melting point: 290° C.

Example (VIII-6)

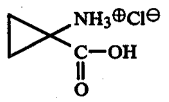

A mixture of 19.4 g (0.15 mol) of α-formylamino-cyclopropanecarboxylic acid and 200 ml of 18% strength hydrochloric acid was heated to the boil under reflux for 3 hours. The mixture was then evaporated to dryness in vacuo, and the residual solid was dried over phosphorus pentoxide in a vacuum desiccator. Yield: 18 g (92% of theory) of α-amino-cyclopropanecarboxylic acid hydrochloride. Melting point: 232° C.

Example (VIII-7)

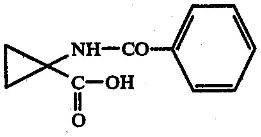

3.1 g (0.022 mol) of benzoyl chloride were added to a mixture of 2 g (0.02 mol) of α-aminocyclopropanecarboxylic acid, 25 ml of water and 2.55 g (0.044 mol) of potassium hydroxide at 20° C., while stirring. After the mixture had been stirred for 30 minutes, it was acidified with concentrated hydrochloric acid to a pH of 1, and was filtered under suction. The product was purified by boiling with 30 ml of water. Yield: 2.1 g (51% of theory) of α-benzylaminocyclopropanecarboxylic acid. Melting point 209° C.

The compounds of the formula

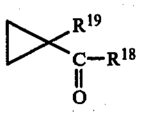

(VIII)

which are listed in Table 6 which follows, were prepared in an analogous manner:

TABLE 6

| Example No. | $R^{18}$ | $R^{19}$ | Yield (% of theory) | Refractive index $n_D^{20}$; melting point (°C.) or boiling point (°C./mbar) |
|---|---|---|---|---|
| VIII-8 | $OCH_2$— 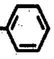 | NHCHO | 74 | 1.5079 |
| VIII-9 | $O^{\ominus}HN(C_2H_5)_3^{\oplus}$ | NHCHO | 85 | 1.4461 |
| VIII-10 | $OC_2H_5$ | NHCHO | 71 | 110/0.1 |
| VIII-11 | $NH_2$ | NHCHO | 70 | 145 |
| VIII-12 | $OCH_3$ | $NH_3^{\oplus}Cl^{\ominus}$ | 81 | 180 |
| VIII-13 | $OCH_3$ | $NH_2$ | 77 | 1.4491 |
| VIII-14 | $OCH_2$— 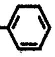 | $NH_3^{\oplus}Cl^{\ominus}$ | 51 | 92 |
| VIII-15 | $OCH_2$— 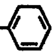 | $NH_2$ | 86 | 1.4849 |
| VIII-16 | $O^{\ominus}Na^{\oplus}$ | $NH_2$ | 97 | 216 |
| VIII-17 | OH | $NH_2$ | 75 | 220 |
| VIII-18 | $OC_2H_5$ | $NH_3^{\oplus}Cl^{\ominus}$ | 83 | 108 |
| VIII-19 | $OC_2H_5$ | $NH_2$ | 75 | 1.4440 |
| VIII-20 | $O^{\ominus}K^{\oplus}$ | $NHCOCH_3$ | 82 | 246 |
| VIII-21 | $OC_2H_5$ | $NHCOCH_3$ | 90 | 76 |
| VIII-22 | $O(CH_2)_7CH_3$ | NHCHO | 95 | 1.4321 |
| VIII-23 | $O(CH_2)_7CH_3$ | $NH_3^{\oplus}Cl^{\ominus}$ | 91 | 1.4429 |
| VIII-24 | $O^{\ominus}Na^{\oplus}$ | NHCHO | 90 | 221 |

It will be appreciated that the instant specification and examples are set forth by way of illustration and not limitation, and that various modifications and changes may be made without departing from the spirit and scope of the present invention.

We claim:

1. A plant growth-regulating composition consisting essentially of a plant growth-inhibiting effective amount of (1)

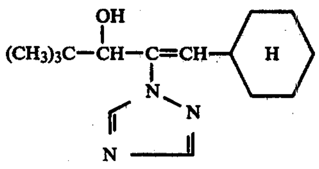

and about 0.5 to 4 times its weight of (2) a 1-amino-cyclopropane-1-carboxylic acid derivative selected from the group consisting of

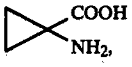

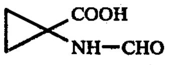

and

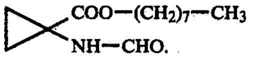

2. A composition according to claim 1, wherein (2) is

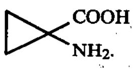

3. A composition according to claim 1, wherein (2) is

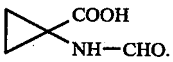

4. A composition according to claim 1, wherein (2) is

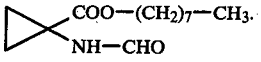

5. A method of regulating the growth of cereal plants which comprises applying to the plants, or to a habitat thereof, a plant growth-inhibiting effective amount of a composition according to claim 1.

6. A method according to claim 5, wherein the composition is applied to an area of agriculture in an amount of about 0.01 to 50 kg. per hectare.

* * * * *

UNITED STATES PATENT AND TRADEMARK OFFICE
CERTIFICATE OF CORRECTION

PATENT NO. : 4,452,625

DATED : June 5, 1984

INVENTOR(S) : Klaus Lurssen et al

It is certified that error appears in the above-identified patent and that said Letters Patent is hereby corrected as shown below:

| | |
|---|---|
| Under "Foreign Patent Documents" | Eighth line insert --DE-- before "2906061" |
| Col. 3, line 25 | Delete "phosphoric" and substitute --phosphonic-- |
| Col. 8, line 13 | Delete "$Y^1$" and substitute --$Y^3$-- |
| Col. 11, 12, 13, 14 and 13, line 1 of each | Insert column headings: --$R^3$ $R^4$ $R^5$ -- |
| Col. 14, 15, 16 | Insert column headings: --$R^3$ $R^4$ $R^5$ $R^8$ -- |
| Col. 17, 18, 19, 20, 21, and 22 | Insert column headings: --$R^3$ $R^4$ $R^5$ $R^7$ $R^8$ -- |
| Col. 21, 6th formula, second column | Delete ""Cyclohexane" and substitute --Cyclohexene-- |
| Col. 40, line 60 | Delete "represent" and substitute --represents-- |
| Col. 41, line 1 | Delete "$M^{61}$" and substitute -- $M^{\oplus}$ -- |
| Col. 41, line 12 | Delete "$-NH_3Cl^{\ominus}$" and substitute -- $-\overset{\oplus}{N}H_3Cl^{\ominus}$ -- |
| Col. 41, line 18 | Delete "1" second instance and substitute --2-- |
| Col. 41, line 50 | Delete "exhibits" and substitute --exhibit-- |
| Col. 42, line 39 | Delete "temperatures" and substitute --temperature-- |
| Col. 43, line 65 | Delete "syneergistic" and substitute --synergistic-- |

UNITED STATES PATENT AND TRADEMARK OFFICE
CERTIFICATE OF CORRECTION

PATENT NO. : 4,452,625

DATED : June 5, 1984

INVENTOR(S) : Klaus Lurssen et al

It is certified that error appears in the above-identified patent and that said Letters Patent is hereby corrected as shown below:

Col. 47, line 38 — Center "Example 11"

Col. 59, 60, 61, 62, 63, 64, 65 and 66, line 1 of each — Insert column headings:

--Example No. $R^3$ $X^1$ $R^4$ $R^5$ Melting point (°C.) --

Col. 59, last line — Delete

" 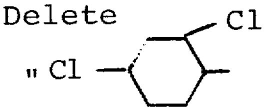 "

and substitute

-- 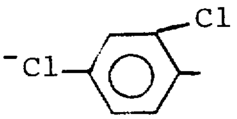 --

Col. 61, line 1, 4th column — Delete "$C_2H_7$" and substitute --$C_2H_5$--

Col. 67, line 12 — Delete "giving" and substitute --given--

Col. 67, line 45 — After "3" insert -- - --

Col. 68, line 53 — After "4.11" delete "mol" and substitute --mmol--

Col. 71, and 72 — Insert column headings:

--Example No. $R^9$ $Y^1$ $X^3$ $Y^3$ Melting point (°C.) or refractive index ($n_D$20)--

UNITED STATES PATENT AND TRADEMARK OFFICE

CERTIFICATE OF CORRECTION

PATENT NO. : 4,452,625

DATED : June 5, 1984

INVENTOR(S) : Klaus Lurssen et al

It is certified that error appears in the above-identified patent and that said Letters Patent is hereby corrected as shown below:

| | |
|---|---|
| Col. 71, line 40 | Delete "refulx" and substitute --reflux-- |
| Col. 72, line 61 | Delete "solutin" and substitute --solution-- |
| Col. 75, line 32 | After "-ol" insert a space |
| Col. 77, line 21 | After "α" insert -- - -- |

Signed and Sealed this

*Twenty-fifth* Day of *December 1984*

[SEAL]

*Attest:*

GERALD J. MOSSINGHOFF

*Attesting Officer*

*Commissioner of Patents and Trademarks*